US007598042B2

(12) United States Patent
Getzenberg

(10) Patent No.: US 7,598,042 B2
(45) Date of Patent: Oct. 6, 2009

(54) EARLY PROSTATE CANCER ANTIGENS (EPCA), POLYNUCLEOTIDE SEQUENCES ENCODING THEM, AND THEIR USE

(75) Inventor: Robert H. Getzenberg, Pittsburgh, PA (US)

(73) Assignee: University of Pittsburgh of the Commonwealth System of Higher Education, Pittsburgh, PA (US)

( * ) Notice: Subject to any disclaimer, the term of this patent is extended or adjusted under 35 U.S.C. 154(b) by 331 days.

(21) Appl. No.: 10/514,735

(22) PCT Filed: Mar. 1, 2004

(86) PCT No.: PCT/US2004/006137

§ 371 (c)(1),
(2), (4) Date: Jan. 20, 2006

(87) PCT Pub. No.: WO2004/078123

PCT Pub. Date: Sep. 16, 2004

(65) Prior Publication Data

US 2006/0148011 A1    Jul. 6, 2006

Related U.S. Application Data

(63) Continuation-in-part of application No. 10/375,058, filed on Feb. 28, 2003, now abandoned.

(51) Int. Cl.
*G01N 33/53* (2006.01)
*C12Q 1/00* (2006.01)
*G01N 33/574* (2006.01)

(52) U.S. Cl. .............................. 435/7.1; 435/4; 435/7.23
(58) Field of Classification Search ........................ None
See application file for complete search history.

(56) References Cited

U.S. PATENT DOCUMENTS

| | | | |
|---|---|---|---|
| 4,882,268 A | 11/1989 | Penman et al. | |
| 4,885,236 A | 12/1989 | Penman et al. | |
| 5,273,877 A | 12/1993 | Fey et al. | |
| 5,308,835 A | 5/1994 | Clements | |
| 5,547,928 A | 8/1996 | Wu et al. | |
| RE35,747 E | 3/1998 | Penman et al. | |
| 5,824,490 A | 10/1998 | Coffey et al. | |
| 5,849,509 A | 12/1998 | Coffey et al. | |
| 5,866,535 A | 2/1999 | Getzenberg et al. | |
| 5,874,539 A | 2/1999 | Coffey et al. | |
| 5,989,826 A | 11/1999 | Beausang et al. | |
| 6,132,968 A * | 10/2000 | Le et al. .................... | 435/6 |
| 6,162,608 A | 12/2000 | Beausang et al. | |
| 6,174,528 B1 | 1/2001 | Cooper et al. | |
| 6,410,247 B1 | 6/2002 | Beausang et al. | |
| 2003/0228640 A1 | 12/2003 | Getzenberg | |

FOREIGN PATENT DOCUMENTS

| | | |
|---|---|---|
| JP | 5-146294 | 6/1993 |
| WO | WO 87/03910 | 7/1987 |
| WO | WO 93/09437 | 5/1993 |
| WO | WO 94/00573 | 1/1994 |
| WO | WO 94/18222 | 8/1994 |
| WO | WO 95/16919 | 6/1995 |
| WO | WO 97/16206 | 9/1997 |
| WO | WO 01/29218 A | 4/2001 |

OTHER PUBLICATIONS

Getzenberg et al., Cancer Res. vol. 51, p. 6514-6520, 1991.*
search result-1.*
search result Le et al.*
Getzenberg et al., Cancer Res. vol. 51, p. 6514-6520, 1991.*
search result-1 (2008).*
search result Le et al., (2008).*
MPSRCH search result, 2007, us-11-080-836.5.rpr.result 3.
MPSRCH search result, 2007, us-11-080-836.5.max_30.rai, result 36.
International Search Report.
Database Genbank pBlueskript KS+ Jan. 29, 2002, XP002292954, Retrieved from NCBI Database accession No. X52331, Nucleotides 772-1287 encode a polypeptide matching amino acids 23-194 of Seq ID 6 *Abstract.
Konety B R et al. "Characterization of a metastatic Dunning rat prostate tumor specific nuclear matrix protein (NMP) AM-1", Proceedings of the Annual Meeting of the American Association for Cancer Research, New York NY US, vol. 37, 1996, p. 73, XP002172068, ISSN: 0197-016X, Abstract.
Anderson et al., "Qualitative Analysis of Coomassie-Blue-Stained Proteins From Normal Prostate, Benign Prostatic Hypertrophy, or Adenocarcinoma of the Prostate, Separated by Two-Dimensional Protein Electrophoresis," *The Prostate*, 1985, pp. 315-323, vol. 6.
Bejany, D.E., et al., Malignant Vesical Tumors Following Spinal Cord Injury, *The Journal of Urology*, vol. 138, pp. 1390-1392 (1987).
Berezney, R., et al., "Identification of a Nuclear Protein Matrix", *Biochemical and Biophysical Research Communications*, vol. 60, No. 4 (1974).
Cech, T.R., PhD., "Ribozymes and Their Medical Implications", *JAMA*, vol. 260, No. 20, pp. 3030-3034 (1988).

(Continued)

*Primary Examiner*—Larry R. Helms
*Assistant Examiner*—Lei Yao
(74) *Attorney, Agent, or Firm*—Stephen A. Bent; Shaun R. Snader; Foley & Lardner LLP

(57) ABSTRACT

A novel prostate cancer marker is described that is found in cancerous and normal prostate cells of individuals that have prostate cancer but is not found in the prostate of individuals without prostate cancer. The marker also is present in normal tissue adjacent to tumor tissue in individuals having prostate cancer. The marker, however, is absent in the prostate of individuals without prostate cancer. Methods employing the novel prostate cancer marker of the invention to predict the occurrence of the prostate disease, monitor the progression of prostate cancer and effect the treatment of prostate cancer, also are described.

6 Claims, 5 Drawing Sheets

OTHER PUBLICATIONS

Celis et al., "Expression of the transformation-sensitive protein "cyclin" in normal human epidermal basal cells and simian virus 40-transformed keratinocytes," Proc. Natl Acad. Sci. USA, vol. 81, pp. 3128-3132 (1984).

Celis et al., "Intermediate filaments in monkey kidney TC7 cells: Focal centers and interrelationship with other cytoskeletal systems," Proc. Natl Acad. Sci. USA, vol. 81, pp. 1117-1121 (1984).

Cupo, J., "Electrophoretic analysis of nuclear matrix proteins and the potential clinical applications", Elsevier Science Publishers B. V., pp. 389-406 (1991).

Diener, E., et al., "Specific Immunosuppression by Immunotoxins Containing Daunomycin", Science, vol. 231, pp. 148-150 (1986).

DiScipio et al., "Nucleotide sequence of cDNA and derived amino acid sequence of human complement component C9," Proc. Natl Acad. Sci. USA, vol. 81, pp. 7298-7302 (1984).

Douillard et al., "Monoclonal Antibodies Specific Immunotherapy of Gastrointestinal Tumors," Hybridoma, vol. 5, Suppl. 1 (1986) pp. S139-S149.

Eberharter A., et al., "Nuclear Matrix of the lower eukaryote *Physarum polycephalum* and the mammalian epithelial $LLC-PK_1$ cell line—A comprehensive investigation of different preparation procedures", vol. 212, No. 2 pp. 573-580 (1992). (XP02068893).

El-Masri, W.S., "Bladder Cancer After Spinal Cord Injury", International Medical Society of Paraplegia, pp. 265-270 (1981).

Fey, E.G., et al., "Epithelial Cytoskeletal Framework and Nuclear Matrix-Intermediate Filament Scaffold: Three-dimensional Organization and Protein Composition", The Journal of Cell Biology, vol. 98, pp. 1973-1984 (1984).

Fey, E.G., et al., "Nuclear matrix proteins reflect cell type of origin in cultured human cells", Proc. Natl. Acad. Sci. USA, vol. 85, pp. 121-125 (1988).

Fey, E.G., et al., "The Nuclear Matrix: Defining Structural and Functional Roles", Eukaryotic Gene Expression, pp. 127-143 (1991).

Fey, E.G., et al., "Tumor promoters induce a specific morphological signature in the nuclear matrix-intermediate filament scaffold of Madin-Darby canine kidney (MDCK) cell colonies", Proc. Natl. Acad. Sci. USA, vol. 81, pp. 4409-4413 (1984).

Fradet Y., "Molecular and immunologic approaches in the management of bladder cancer," Urologic Clinics of North America, vol. 18, No. 3, pp. 515-524 (1991) (XP000881253).

Fraley et al., "New Generation liposomes: the engineering of an efficient vehicle for intracellular delivery of nucleic acids," Trends Biochem. Sci., vol. 6, pp. 77-80 (1981).

Geisler, W.O., et al., "Survival in Traumatic Transverse Myelitis", Paraplegia, vol. 14, pp. 262-275 (1977).

Getzenberg et al., "Modifications of the Intermediate Filament and Nuclear Matrix Networks by the Extracellular Matrix," Biochemical and Biophysical Research Communications, Aug. 30, 1991, pp. 340-344, vol. 179, No. 1.

Getzenberg et al., "Tissue Specificity on the Hormonal Response in Sex Accessory Tissues Is Associated with Nuclear Matrix Protein Patterns," Mol. Endo., 1990, pp. 1336-1342, vol. 4, No. 9.

Getzenberg, R. H., "Nuclear Matrix and the Regulation of Gene Expression: Tissue Specificity", Journal of Cellular Biochemistry, vol. 55, pp. 22-31 (1994).

Getzenberg, R., et al., "Bladder Cancer-associated Nuclear Matrix Proteins", Cancer Research vol. 56, No. 7, pp. 1690-1694, (1996). (XP002068894).

Getzenberg, R.H., et al., "Identification of Nuclear Matrix Proteins in the Cancer and Normal Rat Prostate", Cancer Research, vol. 51, pp. 6514-6520 (1991).

Gordon, J.N., et al., "Altered Extracellular Matrices Influence Cellular Processes and Nuclear Matrix Organizations of Overlying Human Bladder Urothelial Cells", Cancer Research, vol. 53, pp. 4971-4977 (1993).

Greiner, J.W., "Recombinant Interferon Enhances Monoclonal Antibody—Targeting of Carcinoma Lesions in Vivo", Reports, pp. 895-898 (1987).

Hackler, R.H., "A 25-Year Prospective Mortality Study In The Spinal Cord Injured Patient: Comparison With The Long-Term Living Paraplegic", The Journal of Urology, vol. 117, pp. 486-488 (1977).

Haseloff, J., et al., "Simple RNA enzymes with new and highly specific endoribonuclease activities", Nature, vol. 334, pp. 585-591 (1988).

Huse, W.D., et al., "Generation of a Large Combinatorial Library of the Immunoglobulin Repertoire in Phage Lambda", Research Article, pp. 1275-1281 (1989).

Kaufman, J.M., et al., "Bladder Cancer and Squamous Metaplasia in Spinal Cord Injury Patients", pp. 967-971 (1977).

Keesee, S.K., et al., "Utilization of Nuclear Matrix Proteins for Cancer Diagnosis", Critical Reviews in Eukaryotic Gene Expression, vol. 6, No. 2&3, pp. 189-214 (1996). (XP002069158).

Kingsley E.A. et al., "Characterisation of the anti-bladder-cancer monoclonal antibody BLCA—8: identification of its antigen as a neutral glycolipid," Cancer Immunology, Immunotherapy, vol. 41, No. 6, pp. 348-354 1995) (XP000872998).

Konety et al., "Characterization of a Metastatic Dunning Rat Prostate Tumor Specific Nuclear Matrix Protein (NMP) AM-1", Proceedings of the American Association For Cancer Research, vol. 37, p. 73, (1996) (Abstract).

Konety, B.R., et al., "Characteristic Nuclear Matrix Protein Alterations In Renal Cell Carcinoma (RCC)". ). $92^{nd}$ Annual Meeting of the American Urological Association, New Orleans, LA, USA (1997) J. of Urol., vol. 157 (4 suppl.) (1997) (XP-002076375).

Konety, B.R., et al., "Identification of Nuclear Matrix Protein Alterations Associated with Renal Cell Carcinoma", The Journal of Urology, vol. 159, No. 4, pp. 1359-1363 (1998). (XP002068895).

Matritech, NMP22® Test Kit (Jun. 1996) pp. 1-39.

Merrifield, "Solid Phase Peptide Synthesis. I. The synthesis of a Tetrapeptide," J. Am. Chem. Soc., vol. 85, No. 14, pp. 2149-2154 (1963).

Merrifield, S., et al., "The Performance of the NMP22™ Test Kit: A Quantitative Enzyme Immuno-Assay for Bladder Cancer", Tumor Biology, 17 (suppl 1) (1996). (XP-002068915).

Miller et al., "Detection of Nuclear Matrix Proteins in Serum from Cancer Patients," Cancer Research, Jan. 15, 1992, pp. 422-427, vol. 52.

Mullinax, R.L., et al., "Identification of human antibody fragment clones specific for tetanus toxoid in a bacteriophage λ immunoexpression library", Proc. Natl. Acad. Sci. USA, vol. 87, pp. 8095-8099 (1990).

Nyquist, R.H., M.D., et al., "Mortality and Survival in Traumatic Myelof During Nineteen Years, from 1946 to 1965", Paraplegia, pp. 22-48.

Partin et al., "Benign and Malignant Prostatic Neoplasms: Human Studies," Recent Progress In Hormone Research, 1992, pp. 293-331, vol. 49, Academic Press, Inc.

Partin, A.W., et al., "Nuclear Matrix Protein Patterns in Human Benign Prostatic Hyperplasia and Prostate Cancer", Cancer Research, vol. 53, pp. 744-746 (1993).

Pienta et al., "A Common Set of Nuclear Matrix Proteins in Prostate Cancer Cells", The Prostate, vol. 23, pp. 61-67, (1993).

Pirtskalaishvili G. et al., "Use of urine-based markers for detection and monitoring of bladder cancer," Techniques in Urology, vol. 5, No. 4, pp. 179-184 (1999) (XP000881344).

Pound, C.R., et al., "Differential Nuclear Matrix Protein (NMP) Patterns In Normal Renal Tissue And Renal Cell Carcinoma (RCC)". $92^{nd}$ Annual Meeting of the American Urological Association, New Orleans, LA, USA (1997) J. of Urol., vol. 157 (4 suppl.) (1997) (XP-002076374.

Replogle-Schwab R. et al., "The utilization of nuclear matrix proteins for cancer diagnosis," Critical Reviews in Eukaryotic Gene Expression, vol. 6, Nos. 2-3, pp. 103-113 (1996) (XP000881255).

Russell, P.J. et al., "Preclinical studies of monoclonal antibodies for intravesical radioimmunotherapy of human bladder cancer," Cell biophysics, vols. 24/25, pp. 155-161 (1994).

Stewart and Young, "Solid Phase Peptide Synthesis," Freeman Publ. 1969, pp. 27-61.

Weidner, N., et al., "Rapid Communication, Localization of Nuclear Matrix Proteins (NMPs) in Multiple Tissue Types with NM-200.4™ (An Antibody Strongly Reactive with NMPs Found in Breast Carcinoma)", American Journal of Pathology, vol. 138, No. 6, pp. 1293-1298 (1991).

Weintraub, H.M., "Antisense RNA and DNA", *Scientific American*, pp. 40-46 (1990).

Wolff, B., et al., "The Use of Monoclonal Anti-Thy$_1$IgG$_1$ for the Targeting of Liposomes to AKR-A Cells In Vitro and in Vivo", *Biochimica et Biophysica Acta*, vol. 802, pp. 259-273 (1984).

Yanisch-Perron et al., "Improved M13 phage cloning vectors and host strains: nucleotide sequences of the M13mp18 and pUC19 vectors," *Gene*, 1985, pp. 103-119, vol. 33, Elsevier Science Publishers.

Dhir et al., "Early identification of individuals with prostate cancer in negative biopsies", *The Journal of Urology*, vol. 171, pp. 1419-1423 (2004).

Dhir, R., et al., Identification of individuals with prostate cancer by examination of ³negative biopsies², American Urological Association, Annual Meeting, San Francisco, CA, 2004.

Veitmeier, B.N., et al., Early identification of individuals with prostate cancer by examination of ³negative biopsies², Society for Basic Urologic Research Fall Symposium, Tucson, Arizona, 2002.

Getzenberg, R.G., The role of the nuclear matrix and cytoskeleton in cancer, In: Chung, L.W.K., et al. (eds.) Prostate Cancer: Biology, Genetics, and the New Therapeutics. Humana Press, Totowa, NJ. 2000.

Konety, B.R., and R.H. Getzenberg, Nuclear structural proteins as biomarkers of cancer, Journal of Cellular Biochemistry Supplements 32/33:183-191, 1999.

J. Melzak, "The Incidence of Bladder Cancer in Paraplegia", Paraplegia, Aug. 1966, (2):85-96.

Uh Stroeher et al., "In *Vibrio cholerne* serogroup O1, *rfaD* is closely linked to the *rfb* operation", Gene, 1995, Mar 21;155(1); 67-72.

Kenneth L. Bost et al., "Antibodies Against a Peptide Sequence within the HIV Envelope Protein Crossreacts with Human Interleukin-2", Immunological Investigation, 17 (6&7) (1988) pp. 577-586.

N. Miyanaga et al., "Nuclear Matrix Proteins as a Urine Marker for Transitional Cell Carcinoma of the Bladder", The Journal of Urology Supplement vol. 153, No. 4, (XP-002068914) 1995, p. 457A.

International Search Report (2004).

Database Genbank pBlueskript KS+ Jan. 29, 2002, XP002292954, Retrieved from NCBI Database accession No. X52331, Nucleotides 772-1287 encode a polypeptide matching amino acids 23-194 of Seq ID 6 * Abstract.

Konety B R et al. "Characterization of a metastatic Dunning rat prostate tumor specific nuclear matrix protein (NMP) AM-1", Proceedings of the Annual Meeting of the American Association for Cancer Research, New York NYUS, vol. 37, 1996, p. 73, XP002172068, ISSN: 0197-016X, Abstract.

* cited by examiner

SEQUENCE LISTING

```
<160> NUMBER OF SEQ ID NOS: 7

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Ser Asn Thr Pro Leu Pro Gly Val Phe Thr Lys
  1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Ile Gly Asp Asn Gln Lys
  1               5

<210> SEQ ID NO 3
<211> LENGTH: 8
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 3

Asp Ala Tyr Pro Gly Gln Ile Ser
  1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Ser Gly Gln Gly Tyr
  1               5

<210> SEQ ID NO 5
<211> LENGTH: 63
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)
<223> OTHER INFORMATION: Any amino acid
<220> FEATURE:
<221> NAME/KEY: MOD_RES
<222> LOCATION: (38)
<223> OTHER INFORMATION: Any amino acid
<220> FEATURE:
<221> NAME/KEY: MOD_RES
<222> LOCATION: (40)
<223> OTHER INFORMATION: Any amino acid

<400> SEQUENCE: 5

Glu Phe Ser Gly Arg Glu Phe Ala Leu Val Ser Asn Thr Pro Leu Pro
  1               5                  10                  15

Gly Val Leu Thr Lys Lys Gly Glu Phe Val Xaa Thr Cys Arg Thr Ser
                 20                  25                  30

Pro Phe Ser Glu Gly Xaa Phe Xaa Ala Trp Arg Asn His Gly His Ser
             35                  40                  45

Cys Phe Leu Cys Glu Ile Val Ile Arg Ser Gln Phe His Thr Thr
         50                  55                  60

<210> SEQ ID NO 6
<211> LENGTH: 278
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)
<223> OTHER INFORMATION: Any amino acid
<220> FEATURE:
<221> NAME/KEY: MOD_RES
<222> LOCATION: (38)
<223> OTHER INFORMATION: Any amino acid
<220> FEATURE:
<221> NAME/KEY: MOD_RES
<222> LOCATION: (40)
<223> OTHER INFORMATION: Any amino acid
<220> FEATURE:
<221> NAME/KEY: MOD_RES

```
<222> LOCATION: (69)
<223> OTHER INFORMATION: Any amino acid
<220> FEATURE:
<221> NAME/KEY: MOD_RES
<222> LOCATION: (79)
<223> OTHER INFORMATION: Any amino acid
<220> FEATURE:
<221> NAME/KEY: MOD_RES
<222> LOCATION: (84)
<223> OTHER INFORMATION: Any amino acid
<220> FEATURE:
<221> NAME/KEY: MOD_RES
<222> LOCATION: (146)
<223> OTHER INFORMATION: Any amino acid
<220> FEATURE:
<221> NAME/KEY: MOD_RES
<222> LOCATION: (207)
<223> OTHER INFORMATION: Any amino acid
<220> FEATURE:
<221> NAME/KEY: MOD_RES
<222> LOCATION: (246)
<223> OTHER INFORMATION: Any amino acid
<220> FEATURE:
<221> NAME/KEY: MOD_RES
<222> LOCATION: (250)
<223> OTHER INFORMATION: Any amino acid
<220> FEATURE:
<221> NAME/KEY: MOD_RES
<222> LOCATION: (267)..(268)
<223> OTHER INFORMATION: Any amino acid

<400> SEQUENCE: 6

Glu Phe Ser Gly Arg Glu Phe Ala Leu Val Ser Asn Thr Pro Leu Pro
 1               5                  10                  15

Gly Val Leu Thr Lys Lys Gly Glu Phe Val Xaa Thr Cys Arg Thr Ser
            20                  25                  30

Pro Phe Ser Glu Gly Xaa Phe Xaa Ala Trp Arg Asn His Gly His Ser
        35                  40                  45

Cys Phe Leu Cys Glu Ile Val Ile Arg Ser Gln Phe His Thr Thr Tyr
    50                  55                  60

Glu Pro Glu Ala Xaa Ser Val Lys Pro Gly Val Pro Asn Glu Xaa Ala
65                  70                  75                  80

Asn Ser His Xaa Leu Arg Cys Ala His Cys Pro Leu Ser Ser Arg Glu
                85                  90                  95

Thr Cys Arg Ala Ser Cys Ile Asn Glu Ser Ala Asn Ala Arg Gly Glu
            100                 105                 110

Ala Val Cys Val Leu Gly Ala Leu Pro Leu Pro Arg Ser Leu Thr Arg
        115                 120                 125

Cys Ala Arg Ser Phe Gly Cys Gly Glu Arg Tyr Gln Leu Thr Gln Arg
    130                 135                 140

Arg Xaa Tyr Gly Tyr Pro Gln Asn Gln Gly Ile Thr Gln Glu Arg Thr
145                 150                 155                 160

Cys Glu Gln Lys Ala Ser Lys Arg Pro Gly Thr Val Lys Arg Pro Arg
                165                 170                 175

Cys Trp Arg Phe Ser Ile Gly Ser Ala Pro Leu Thr Ser Ile Thr Lys
            180                 185                 190

Ile Asp Ala Gln Val Arg Gly Gly Glu Thr Arg Gln Gly Leu Xaa Arg
        195                 200                 205

Tyr Gln Ala Phe Pro Pro Gly Ser Ser Leu Val Arg Ser Pro Val Pro
    210                 215                 220

Thr Pro Ala Ala Tyr Arg Ile Pro Val Arg Leu Ser Pro Phe Gly Lys
225                 230                 235                 240

Arg Gly Ala Phe Ser Xaa Leu Thr Leu Xaa Val Ser Gln Phe Gly Val
```

-continued

```
                245                 250                 255
Gly Arg Ser Leu Gln Leu Gly Cys Val His Xaa Xaa Pro Val Gln Pro
            260                 265                 270
Asp Ala Ala Pro Tyr Pro
        275

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Ser Asn Thr Pro Leu Pro Gly Val Leu Thr Lys
  1               5                  10
```

EARLY PROSTATE CANCER ANTIGENS (EPCA), POLYNUCLEOTIDE SEQUENCES ENCODING THEM, AND THEIR USE

CROSS-REFERENCE TO RELATED PATENT APPLICATIONS

This application is a continuation-in-part of U.S. application Ser. No. 10/375,058, filed Feb. 28, 2003, which is a continuation-in-part of U.S. application Ser. No. 09/418,839, filed Oct. 15, 1999.

STATEMENT REGARDING GOVERNMENT SPONSORED RESEARCH

This invention was made with support from the National Cancer Institute under grant No. R29 CA65463-01. Thus, the government may have certain rights to this invention.

FIELD OF THE INVENTION

This invention relates generally to compositions and methods for detecting cancer in mammals, including humans. More particularly, the invention relates to the use of a protein, herein designated early prostate cancer antigen (EPCA), for diagnosing and treating prostate cancer, and to methods of assessing the aggressiveness and metastatic potential of prostate cancer by monitoring the level of EPCA or fragments thereof.

BACKGROUND OF THE INVENTION

Abnormalities of prostate growth, including cancer and benign prostatic hyperplasia (BPH), produce some of the most common, costly, and devastating diseases occurring in men. Prostate cancer has exceeded lung cancer as the most commonly diagnosed cancer among men living in the United States, and is the second leading cause of cancer death in that population. *American Cancer Society*, Cancer Facts and Figures: 2004.

Early diagnosis of prostate cancer is central to effective treatment of the disease. Additionally, the ability to differentiate prostate cancer with metastatic potential from prostate cancer that is unlikely to metastasize is important.

Nuclear structural alterations are so prevalent in cancer cells that they are pathological markers of transformation for many types of cancer. Nuclear shape reflects the internal nuclear structure and processes, and is determined, at least in part, by the nuclear structure. Pienta, K. J. et al., *Cancer Research* 49:2525-2532 (1989). Structural components of the nucleus also play a central role in regulating important cellular processes such as DNA replication and transcription. Getzenberg, R. H. *J Cell. Biochem.* 55:22-31 (1994). The nuclear matrix is the framework; or scaffolding, of the nucleus, and consists of peripheral laminins, pore complexes, an internal ribonucleic protein network, and residual nucleoli (Berezney, R. and Coffey, D. S. *Biochem. Biophys. Res. Comm.* 60:1410-1417 (1974). It constitutes approximately 10% of the nuclear proteins and is virtually devoid of lipids, DNA and histones (Fey, E. G. et al., *Critical Rev. in Eukaryotic Gene Expression* 1:127-144 (1991).

Berezney first showed, while examining hepatoma nuclear matrix proteins (NMPs), that the nuclear matrix is altered in transformation. Berezney et al., *Cancer Res.* 39:3031-39 (1979). In addition, Fey and Penman demonstrated that tumor promoters induce a specific morphologic signature in the nuclear matrix-intermediate filament scaffold of kidney cells. Fey et al., *Proc. Natl. Acad. Sci. USA* 81:859-66 (1984). Fey and Penman further showed that the pattern of NMPs differed between normal and tumorigenic cell lines. Fey et al., loc. cit. 85:121-25 (1989); U.S. Pat. No. 4,885,236 and Re. 35, 727. Furthermore, an antibody to a nuclear matrix protein, termed NM-200.4, was raised from the breast carcinoma cell line T-47D. Weidner et al., *Am. J. Path.* 138:1293-98 (1991). This antibody reacts strongly with human breast carcinoma specimens as well as specimens from lung, thyroid, and ovarian cancers; however, it does not react with normal epithelial cells of similar origin, thereby raising the possibility of using certain anti-NMP antibodies as diagnostic tools.

While all cell types and physiologic states share the majority of NMDs, some NMPs appear to be unique to certain cell types or states. It has been demonstrated that the protein composition of the nuclear matrix is tissue-specific and represents a "fingerprint" of each cell and/or tissue type (Getzenberg, R. H. and Coffey, D. S. *Mol. Endocrinol.* 4(9):1336-1342 (1990)). Mitogenic stimulation and induction of differentiation alter the composition of nuclear matrix proteins and the resulting structure (Dworetzky, S. I. et al., *Proc. Natl. Acad. Sci. USA* 87:4605-4609 (1990); Stuurman, N. et al., *Exp. Cell Res.* 180:460-466 (1989)). Differences in NMP composition also are found among a number of human tumors, including renal (Konety, B. R. et al., *J. Urol.* 159: 1359-1363 (1998)), breast (Khanuja, P. S et al., *Cancer Res.* 53:3394-3398, (1993)), colon (Keesee, S. K. et al., *Proc. Natl. Acad. Sci. USA* 91:1913-1916 (1994)), and head and neck tumors (Donat, T. L. et al., Otolaryngol. Head Neck Surg. 127:609-622 (1996)); McCaffrey, J. D. et al., *Arch. Otolaryngol. Head Neck Surg.* 123:283-288 (1997)).

U.S. Pat. No. 5,824,490 discloses certain nuclear matrix proteins associated with prostate tissue, including one denoted "PC-1 (prostate cancer-1)," which was used to identify prostate cancer. When human prostate samples were examined, nuclear matrix proteins were identified that (1) were present only in the normal prostate and were missing in both prostate cancer and BPH (normal pattern), (2) were found only in the prostate cancer cells and missing in the normal prostate and BPH (prostate cancer pattern), and (3) were found in both normal and BPH samples but were absent from prostate cancers. PC-1 (molecular weight 56 Kd and isoelectric point 6.58) represents an NMP seen only in human prostate cancer tissue and was consistently absent in all normal prostate and BPH samples.

Getzenberg et al. also reported the existence of an NMP derived from rat prostate, and designated AM-1. Getzenberg et al., *Cancer Res.* 51:6514-20 (1991). AM-1 exists in cancerous Dunning rat prostate tumors, but not in normal prostate, and has a molecular weight of 40 kD and a pI of 6.73. In a later abstract, Getzenberg et al. further characterized AM-1 as an NMP present only in metastatic rat prostate cancer cells, based on antibody studies in metastatic cell lines. Konety et al., *Proc. Am. Assoc. Cancer Res.*, 37:73 (1996).

U.S. Pat. Nos. 5,874,539 and 6,030,793 and U.S. serial application No. 20020168695 disclose the use of proteins as biomarkers for diagnosing and monitoring the stage of malignancy of a prostate cell and for treating prostate cell proliferative disorders associated with the proteins. PC-1 is an example of these protein markers.

U.S. Pat. No. 6,090,559 discloses diagnostic techniques for detecting human prostate cancer through the use of genetic probes and methods. In particular, this patent discloses probes and methods for evaluating the presence of RNA species that are differentially expressed in prostate cancer relative to normal human prostate or benign prostatic hyperplasia.

U.S. serial application No. 20020164664, by Hlavaty, J. J. et al. (Matritech, Inc.), discloses a wide range of methods and compositions for detecting and treating prostate cancer. Specifically, the application provides target prostate cancer-associated proteins, which reportedly permit rapid detection, preferably before the occurrence of metastatic prostate cancer. These proteins are said to be detectable at a higher concentration in the serum of individuals with cancer than in the serum of individuals without cancer. Furthermore, they are said to be detectable at a higher concentration in individuals with disseminated prostate cancer than in individuals with localized (organ-confined) prostate cancer. One of the prostate markers purportedly permits detection of more than 90% of all prostate cancer, including cancers that are undetectable by prostate specific antigen (PSA) assays.

U.S. Pat. Nos. 5,989,826, 6,162,608, and 6,410,247B1 disclose methods for determining the degree of cell death in a tissue by detecting and quantitating soluble "interior" nuclear matrix proteins and protein fragments in body fluids and extracellular media. These methods purportedly are useful for monitoring the viability of cells and tissue, for evaluating the progress of a disease or its treatment, and for evaluating the cytotoxicity of unknown compounds. Also disclosed are methods for inducing the release of "interior" nuclear matrix proteins and protein fragments in soluble form from cells.

The use of prostate specific antigen (PSA) as a marker to screen individuals for prostate cancer has changed management of the disease and has permitted earlier detection in many men. The use of this marker, however, has caused many men to undergo repeated biopsies because of abnormally high PSA levels. Some of these men later prove to have clinical disease, but for many others, high PSA levels do not predict prostate cancer.

Beside the above-mentioned proteins, clinical and pathological staging and histological grading systems (e.g. Gleason's) have been utilized as prognostic indicators for patients, based on tumor differentiation or type of glandular pattern (Carter, H. B. and Coffey, D. S., J. Urol. 140:173-5 (1988)). However, these systems do not predict cancer progression.

As the preceding discussion illustrates, many unanswered questions still exist regarding the molecular etiology of prostate cancer. Current diagnostic and prognostic tools are unable to predict which men with prostate cancer will develop progressive and metastatic disease.

Thus, there remains a need for better prostate cancer biomarkers and for assays that are simple, rapid, sensitive, predictive and inexpensive, within or without clinical settings. There is also a need for diagnostic methods that can distinguish between aggressive and non-aggressive forms of prostate cancer and that can better identify and evaluate hyperplastic and malignant types of prostate cancers, preferably at an earlier stage.

More specifically, a need exists for a prostate biomarker that can identify individuals with prostate cancer even when the individuals' biopsy samples are morphologically negative. There is a also a need for corresponding antibodies, as an adjunct to pathologic examination of prostatic biopsies, to detect prostate cancer earlier, and thereby avoid or reduce the need for repeated biopsies,.

SUMMARY OF THE INVENTION

A novel human protein, designated herein as "early prostate cancer antigen (EPCA)," is expressed throughout the prostate of individuals with prostate cancer and is clinically useful for early detection of individuals with the disease, even in biopsied tissue samples that are morphologically normal. Indeed, the EPCA marker can detect the disease in individuals more than two years prior to morphological manifestation. Thus, anti-EPCA antibodies are useful as an adjunct to pathological examination of prostatic biopsies to detect prostate cancer earlier than using repeated biopsies as well as potentially limiting the number of biopsies in an individual.

The EPCA marker stains both cancerous and normal prostate cells in individuals that have prostate cancer, but is not detected in the prostate of individuals without prostate cancer, where an individual is defined as having prostate cancer if a pathologically identified lesion is present within the individual's prostate. The human EPCA protein corresponds to rat AM-1, disclosed in U.S. Ser. No. 09/418,839, but has a strikingly different expression pattern than all previously described nuclear matrix proteins (NMPs). EPCA predominantly stains outside of the cell nucleus in human prostate, particularly in the cytoplasm and cell membrane. Remarkably, EPCA stains even normal adjacent tissue (NAT) and normal tissue throughout the prostate of an individual with prostate cancer. EPCA therefore appears to represent a different type or class of protein than previously has been described.

In another aspect, the present invention, directed to EPCA, can be employed to predict the occurrence of prostate cancer and to monitor the progression of prostate cancer. EPCA is expressed at higher levels in aggressive prostate cancer than in non-aggressive prostate cancer. It stains the intra-prostatic tissue, the lymph nodes and seminal vesicles of individuals with metastatic prostate cancer. EPCA also is present in normal tissue adjacent to tumor tissue of individuals having prostate cancer. However, EPCA is absent in the prostate of individuals without prostate cancer. Thus, detection methods employing EPCA as a prostate cancer biomarker decrease the risk of false negative biopsy reports due to sampling errors, because EPCA is present in both normal and diseased prostate tissues of individuals having prostate cancer.

According to another aspect, the present invention is directed to EPCA and fragments thereof, which are expressed throughout the prostate of individuals with prostate cancer, even in biopsy samples that are morphologically negative. Surprisingly, EPCA is detectable in the prostate of these individuals at least two years prior to morphological detection of prostate cancer. Antibodies against EPCA or fragments thereof are useful as an adjunct to pathologic examination of prostatic biopsies, to detect prostate cancer earlier, and thus avoid or reduce the need for repeated biopsies.

In one aspect, the invention relates to EPCA having a molecular weight of about 40 kD and a pI of about 6.73.

In another aspect, EPCA comprises the peptide sequence EFSGREFALVSNTPLPGVLTKKGEFV*TCRTSPFSEG*F*AWRNHGHSCFLCEIVIRSQF HTT (SEQ ID NO:5), or EFSGREFALVSNTPLPGVLTKKGEFV*TCRTSPFSEG*F*AWRNHGHSCFLCEIVIRSQF HTTYEPEA*SVKPGVPNE*ANSH*LRCAHCPLSSRET CRASCINESANARGEAVCVLG ALPLPRSLTRCARSFGCGERYQLTQRR*YGYPQNQGI TQERTCEQKASKRPGTVKRP RCWRFSIGSAPLTSITKIDAQVRGGETRQGL*RYQAF PPGSSLVRSPVPTPAAYRIPVR LSPFGKRGAFS*LTL*VSQFGVGRSLQLGCVHPVQPD AAPYP (SEQ ID NO:6), each derived from a human specimen, where * represents an undetermined amino acid. The invention also encompasses polypeptides that contain portions of these sequences.

According to another aspect, the present invention is directed generally to methods for differentiating a metastatic prostate cell from a non-metastatic prostate cell, comprising determining the presence or absence of EPCA or a fragment thereof that is unique to a metastatic cell and thus is absent in normal prostate cells. In a representative embodiment, the methods of the inventions also comprise (1) determining an expression level of prostate specific antigen in the metastatic prostate cancer cell and (2) correlating the expression level with EPCA. Similarly, the methods may comprise (1) determining the Gleason scores of an individual having metastatic prostate cancer and (2) correlating the Gleason scores with EPCA.

Preferably, the fragments of EPCA employed in the methods and compositions of the invention are immunogenic fragments.

Another embodiment of the present invention is a purified polynucleotide sequence encoding EPCA or EPCA fragments thereof. Another embodiment is a purified polynucleotide sequence that hybridizes to the polynucleotide sequence encoding the EPCA or EPCA fragments of the invention.

Another embodiment is a host cell transformed with a polynucleotide sequence encoding the above-mentioned sequences.

Another embodiment is a recombinant expression vector containing the above-mentioned polynucleotide sequences. Preferably, the vector is a virus. Preferred viruses are RNA viruses and preferred RNA viruses are retroviruses. Another preferred vector is a liposome, preferably a target-specific liposome which may be targeted with, for example, an antibody or ligand. Another preferred vector is a plasmid.

Another embodiment is an antibody that binds to the EPCA or EPCA fragments of the invention. The antibody may be polyclonal, monoclonal or an antigen-binding fragment thereof. Such anti-EPCA reagents are capable of differentiating between cancerous prostate tissue and normal prostate tissue in human tissues. One embodiment of the present invention is directed to such antibodies. Furthermore, another embodiment of the present invention is directed to antibodies that are capable of detecting individuals with prostate cancer having the potential to advance and/or metastasize. Yet another embodiment is directed to antibodies capable of detecting individuals at a significant risk for developing morphologically detectable prostate cancer.

Another embodiment is a method for detecting a cell proliferative disorder in a subject or for detecting individuals at risk of developing a cell proliferative disorder, preferably prostate cancer, comprising contacting a cellular component from the subject with an antibody or nucleic acid probe that binds to a cellular component associated with the cell proliferative disorder. More preferably, the method is a method for differentiating between prostate cancer that has the potential to metastasize and prostate cancer that lacks the potential to metastasize. Preferably, the cellular component is taken from the subject's prostate and is preferably a nucleic acid. Preferably, the nucleic acid is DNA encoding the above-mentioned EPCA or EPCA fragments. Also preferred as a nucleic acid is RNA. Another preferred cellular component is the EPCA or EPCA fragments of the invention. The differentiation method may be practiced by detecting a single EPCA fragment and/or its corresponding DNA or a combination of one or more EPCA fragments and/or their corresponding DNA.

Preferably, the nucleic acid probe specifically hybridizes to the above-mentioned cellular component. When the reagent is a nucleic acid probe, it preferably is detectably labeled. Exemplary preferred labels include a radioisotope, a bioluminescent compound, a chemiluminescent compound, a fluorescent compound, a metal chelate, and an enzyme.

Alternatively, if the cellular component is EPCA or an EPCA fragment, then an antibody is used that specifically binds to the EPCA or EPCA fragment. As noted above, the antibody may be monoclonal or polyclonal.

Another embodiment is a method of treating a cell proliferative disorder associated with EPCA that comprises administering to a subject with the disorder a therapeutically effective amount of an antisense polynucleotide sequence that blocks at least part of the sequences encoding the above-mentioned EPCA protein. In this embodiment, the treatment is designed to block EPCA expression, which gives rise to the cell proliferative disorder. More preferably, the method is a method of inhibiting metastasis of a cell proliferative disorder and preferably the disorder is prostate cancer.

In an alternative method of treatment, instead of using an antisense polynucleotide sequence, a polynucleotide sequence is used that encodes EPCA. In this embodiment, the treatment is designed to provide the subject with EPCA that prevents or ameliorates the cell proliferative disorder.

In another method of treatment, an antibody is administered to the subject that is capable of blocking the action of EPCA.

Another embodiment is a method of gene therapy, comprising introducing into the cells of a host subject an expression vector comprising a polynucleotide sequence encoding EPCA or a fragment thereof. Preferably, the expression vector is introduced into the cells of the host subject ex vivo, yielding transformed cells, and the transformed cells then are reintroduced into the subject. A preferred expression vector for this purpose is an RNA virus, preferably a retrovirus.

Another embodiment of the present invention relates to a method for identifying a composition that blocks or enhances the function of a prostate cell EPCA. The inventive method comprises: (a) incubating EPCA-containing prostate cells with a test composition under conditions that allow the prostate cells and test composition to interact, and (b) measuring whether the test composition blocks or enhances the function of the prostate cell EPCA.

Another embodiment of the present invention is a kit for detecting a cell-proliferative disorder of the prostate, comprising an antibody that specifically binds to EPCA or a fragment thereof. Preferably, the antibody is labeled for ease of detection with a label, as described above.

In yet another embodiment, there is a method for determining the presence or absence of metastatic prostate cancer cell in a sample containing nucleic acids, comprising the steps of: (a) hybridizing the complement of a polynucleotide sequence encoding EPCA or said immunogenic fragment thereof, to at least one of the nucleic acids of said sample, thereby forming a hybridization complex; and (b) detecting said hybridization complex, wherein the presence of said hybridization complex correlates with the presence of said sequence encoding EPCA or an immunogenic fragment thereof in said sample. Alternatively, the nucleic acids of the sample are amplified by polymerase chain reaction prior to the hybridizing step with the use of an oligonucleotide primer.

BRIEF DESCRIPTION OF THE DRAWINGS

The antibody employed in FIGS. 1-5 is raised against VSNTPLPGVFTK (SEQ ID NO:1).

FIG. 2 D shows a focus of carcinoma metastasizing to the lymph node with predominant cytoplasmic staining for EPCA.

FIG. 3 shows a panel of immunohistochemical staining of EPCA from donor prostatectomies. FIG. 3A shows a section from a donor prostatectomy with absence of staining for EPCA. FIG. 3B shows a section from an older donor with moderate to strong cytoplasmic staining for EPCA. FIG. 3C shows later evaluation of other sections from the same older donor prostate in FIG. 3B with a focus of high-grade prostatic intra-epithelial neoplasia (PIN).

DETAILED DESCRIPTION OF THE PREFERRED EMBODIMENTS

Figure 1:
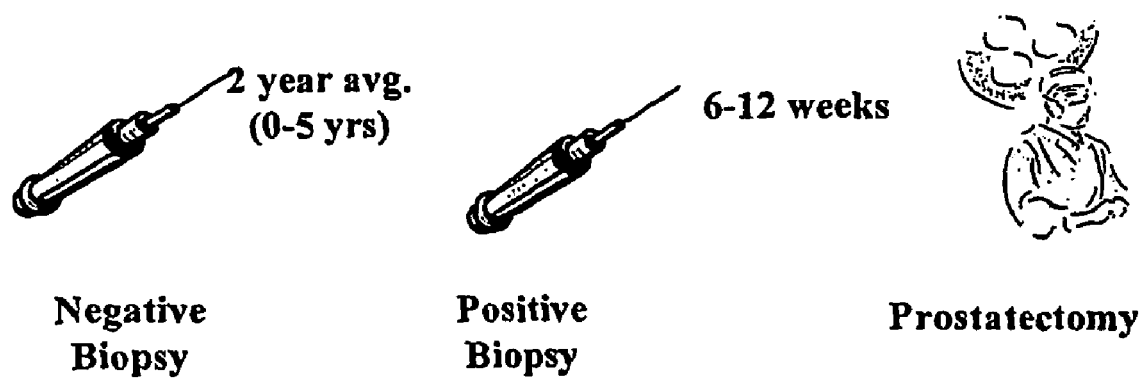
FIG. 1 shows a scheme for a representative EPCA biopsy immunohistochemical study.
Figure 2D:
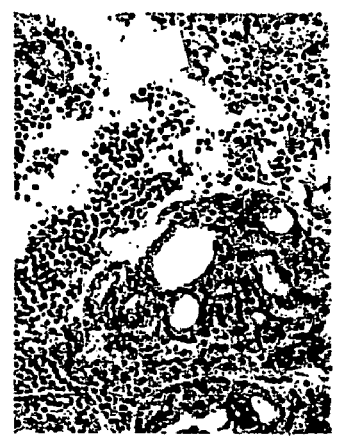
FIG. 2 shows a panel of immunohistochemical staining of EPCA in a patient subsequently diagnosed with carcinoma.
FIG. 2A shows a negative biopsy with strong cytoplasmic staining for EPCA.
FIG. 2B displays a focus of high-grade prostatic intra-epithelial neoplasia (PIN) having cytoplasmic staining for EPCA.
FIG. 2C shows a focus of carcinoma with a predominant strong membrane staining for EPCA and with some cytoplasmic staining.
Figure 2C:
Figure 2B:
Figure 2A:

Unless otherwise specified, "a" or "an" means "one or more".

Definitions

In the description that follows, a number of terms are used. The following definitions of several terms are provided to facilitate understanding of the present invention.

The phrase "purified nuclear matrix protein (purified NMP)" means a protein of the nuclear matrix that has been separated from at least one cellular component. The phrase covers both purified nuclear matrix proteins produced recombinantly and those produced by extraction from a natural source.

The protein of the present invention, human EPCA, and fragments thereof, differ from NMPs of the prior art. Nuclear matrix proteins are classically sequestered within the nucleus. By contrast, EPCA exists only in small quantities within the nucleus of human prostate cancer cells, as determined by cytological staining. Instead, EPCA is found primarily outside of the nucleus, particularly in the cytoplasm and cell membrane. Thus, relative to known NMPs, EPCA has a unique expression pattern.

EPCA may be isolated by a process described in Example 1, below. In brief, lipids and soluble proteins are released from prostate tissue by homogenization in a detergent solution containing an RNase inhibitor. Soluble cytoskeletal elements are then removed by filtration and extraction with ammonium sulfate solution containing an RNase inhibitor. Chromatin is then removed via a DNase treatment, which optionally is followed with an RNase treatment. The remaining fractions contain intermediate filaments and NMPs. These are separated by completely solubilizing all proteins in buffered 5 to 10 M urea, preferably 8 M or as required to completely dissolve the proteins. Solubilization is followed by dialysis of the proteins back into a physiological buffer, which causes intermediate filaments to reassemble. The intermediate filaments subsequently are removed by centrifugation. Finally, NMPs then can be ethanol precipitated and separated by high resolution two-dimensional gel electrophoresis. EPCA has a molecular weight of about 40 kD and a pI of about 6.73.

Amino acid sequences of rat AM-1 peptides include VSNTPLPGVFTK (SEQ ID NO:1), TIGDNQK (SEQ ID NO:2), DAYPGQIS (SEQ ID NO:3), and DSGQGY (SEQ ID NO:4). EPCA peptide sequences, derived from a human specimen, include EFSGREFALVSNTPLPGVLTKKGEFV*TCRTSPFSEG*F*AWRNHGHSCFLCEIVIRSQF HTT (SEQ ID NO:5) and EFSGREFALVSNTPLPGVLTKKGEFV*TCRTSPFSEG*F*AWRNHGHSCFLCEIVIRSQF HTTYEPEA*SVKPGVPNE*ANSH*LRCAHCPLSSRET CRASCINESANARGEAVCVLG ALPLPRSLTRCARSFGCGERYQLTQRR*YGYPQNQGI TQERTCEQKASKRPGTVKRP RCWRFSIGSAPLTSITKIDAQVRGGETRQGL*RYQAF PPGSSLVRSPVPTPAAYRIPVR LSPFGKRGAFS*LTL*VSQFGVGRSLQLGCVHXXPVQ PDAAPYP (SEQ ID NO:6), where * represents any amino acid. The invention encompasses polypeptides that contain these sequences or portions of these sequences, such as 5, 10, 15, 20, 25, 30, 35, 40, 45, 50, 60, 70, 80, 90, 100, 125, 150, 200 or 250 contiguous amino acids of these sequences.

The inventor is not aware of any previously described NMP that shares the unique characteristics of EPCA and its fragments. Thus, EPCA and its fragments are believed to represent members of a novel class of proteins.

The phrase "cell proliferative disorder" denotes malignant as well as non-malignant cell populations that often appear to differ from the surrounding tissue both morphologically and genotypically. Malignancy (i.e., cancer) is a multistep process and involves three broad steps in the transitioning a normal cell to a cancer cell. In broad stages, normal tissue (stage 1) may begin to show signs of hyperplasia (stage 2) or show signs of neoplasia (stage 3).

As used herein, "hyperplasia" refers to cells that exhibit abnormal multiplication or abnormal arrangement in a tissue. Included in the term "hyperplasia," are benign cellular proliferative disorders, including benign tumors.

The term "tissue expression pattern" refers to the synthesis and/or distribution of a gene product of an NMP gene at a level that is detectable by methods commonly used by those of skill in the art (e.g., SDS-polyacrylamide gel electrophoresis).

As used herein, "neoplasia" refers to abnormal new growth, which results in a tumor. Unlike hyperplasia, neoplastic proliferation persists even in the absence of the original stimulus and is characterized as uncontrolled and progressive. Malignant neoplasms, or malignant tumors, are distinguished from benign tumors in that the former show a greater degree of anaplasia and have the properties of invasion and metastasis.

The protein of the present invention, EPCA, is associated with metastatic prostate tumor cells. The term "associated with" refers to the correlation between the expression pattern of the protein and the stage of progression to cancer.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of EPCA that are preferably about 5 to about 15 amino acids in length and that retain some biological activity or immunological activity of EPCA. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

As used herein, the term "biologically active," refers to a protein having structural, regulatory, or biochemical functions of a naturally occurring molecule. Likewise, "immunologically active" refers to the capability of the natural, recombinant, or synthetic EPCA, or of any peptide thereof, to induce a specific immune response in appropriate animals or cells and to bind with specific antibodies.

The phrase "individual without prostate cancer" means that no pathologically identified lesions are present within the prostate of that individual. The phrase "individual having prostate cancer" means that the individual has a pathologically identified lesion within the prostate. The phrase "individual at risk for having prostate cancer" refers to a person having an abnormal PSA value (typically greater than 4 ng/ml) and/or an abnormal digital rectal exam. A pathologist can determine the presence of a pathological lesion within a prostate by biopsy or prostatectomy following an established protocol (see Epstein, J. I. Pathology of Prostatic Neoplasia in Campbell's Urology 8th Edition, Walsh, Retik, Vaughan and Wein (eds.), Saunders, Philadelphia, pp. 3025-3037, 2002).

"Gleason grading system," as defined by Dr. D. F. Gleason in 1974 and 1977, is one of the most commonly used systems to grade the appearance of prostate cancer tissue. It is a strong prognostic indicator and powerful predictor of prostate disease progression. Gleason grading involves making categorizations based on the degree of glandular differentiation and patterns of growth of carcinoma. Gleason grading from very well differentiated (tumor whose structure is nearly normal or Grade I) to very poorly differentiated (Grade 5) is usually performed by viewing a low magnification microscopic image of the cancer. Gleason Grades 1 and 2 closely resemble the normal prostate. Gleason Grade 3, the most common grade, is considered well differentiated. In Grade 4, there is disruption and loss of the normal gland unit resulting in poorly differentiated architecture. Gleason Grade 5 predicts a poor prognosis, and is characterized by cells exhibiting a lack of pattern in nuclear arrangement (undifferentiated), which leads to a total loss of architecture.

"Gleason Score" is written as a sum of the two Gleason patterns/grades, namely primary and secondary patterns. The former being the dominant and most frequent pattern and the latter being the subdominant and second most frequent pattern. For example, a Gleason score of 2+3=5 has a dominant well-differentiated pattern (i.e., Pattern/Grade 2) and a less dominant moderately differentiated pattern (i.e., Pattern/Grade 3). Gleason score is determined by the pathologist who examines prostate biopsies or determines the entire prostate after prostate surgery. Gleason score is one of the strongest prognostic factors available and enables the doctor to decide which treatment may be beneficial. Gleason scores are defined as follows:

| Gleason Score | (GS) |
| --- | --- |
| Low Grade | 2-4 |
| Intermediate Grade | 5-6 |
| Intermediate to High Grade | 7 |
| High Grade | 8-10 |

The immunohistochemical staining of EPCA or serum analysis of EPCA can be used together with Gleason scoring to improve the diagnosis of prostate cancer. Specifically, a Gleason score of 7 poses a problem because the exact determination of prostate cancer is uncertain. Accordingly, a pathologist or urologist can be more certain of the existence of prostate cancer from results obtained using both EPCA diagnosis and Gleason scoring.

The term "prostate specific antigen (PSA)" refers to a protein manufactured in the prostate. It is one of the enzymes responsible for liquefaction of semen a few minutes after it has clotted. PSA levels in the blood rise if the barrier between the epithelium and the blood stream is damaged. Three typical sources are cancer, bacterial infection, and prostate infarction or destruction of part of the prostate by damage to its blood supply. A normal PSA level in the blood is typically considered to be in the range of 0-4 ng/ml. However, there is some consideration to lower the upper part of this range.

There exists a "gray zone" of uncertainty for prostate cancer when the PSA values range from 2.5-10 ng/ml. The combination of determining the level of PSA and EPCA would lower this uncertainty and would result to a better diagnosis of prostate cancer. This can be seen in an individual who has a relatively low, but possibly problematic, serum level of 4 ng/ml, but has a biopsy tissue sample with no detectable EPCA staining (and/or low serum EPCA level). This individual would benefit from periodic PSA and EPCA diagnostic assays. An EPCA serum test may also be employed. In another instance, an individual with a serum PSA level of 4 ng/ml and extensive EPCA tissue biopsy staining (and/or high serum EPCA levels) would benefit from immediate medical attention that may provide alternatives such as surgery or radiation therapy. Therefore, the combinatorial use of both EPCA and PSA diagnostic assays provide an enhanced diagnostic benefit to these individuals.

The term "prostate intraepithelial neoplasia (PIN)" is most likely the precursor of prostatic adenocarcinoma A urologist or pathologist may use the following terms for PIN: dysplasia, intraductal dysplasia, large acinar atypical hyperplasia, atypical primary hyperplasia with malignant change, marked atypia or ductal acinar dysplasia. PIN is divided into low grade (grades I and II) and high grade (grade III) PIN. The significance of low grade PIN is unknown. However, high grade PIN is a known precursor and risk factor for invasive prostatic adenocarcinoma. Identification in biopsies requires a search for invasive carcinoma. When found on transrectal ultrasound (TRUS), the risk of carcinoma on subsequent biopsies is from 27% to 79%.

The term "antibody" as used herein includes antibodies that react with EPCA or with one or more of the peptide fragments of EPCA. The term "antibodies" is also intended to include parts thereof such as Fab, Fv fragments as well as antibodies that react with the overlapping regions of one or more of the peptide fragments of the invention and recombinantly produced fragments and fusion products of antibody fragments (including multivalent and/or multi-specific). The term "antibodies" is also intended to include antibodies to receptors specific for one or more of the peptide fragments of the invention. Antibodies can be fragmented using conventional techniques and the fragments screened for utility in the same manner as described above. Antibodies may be used either for screening for diagnostic purposes or in order to identify additional peptide fragments, mimetics, variants and inhibitors of the invention.

The term "auto-antibody" refers to an antibody obtained from an individual or animal and which is reactive to a normal cellular antigen(s) or a self-antigen from the same individual or animal.

By the terms "functionally equivalent variant" or "variant" is meant minor modifications to the peptides described herein. The terms may include replacement of one or more amino acids with one or more amino acid substitutions, insertions, and/or deletions. Amino acid substitutions may be of a conserved nature or may be non-conserved. Conserved amino acid substitutions may involve replacing one or more amino acids of the proteins of the invention with amino acids of similar charge, size, and/or hydrophobicity characteristics. Non-conservative substitutions involve replacing one or more amino acids that possess dissimilar charge, size, and/or hydrophobicity characteristics. Variants also include post translational modifications to the peptide fragments, including enzymatic and non-enzymatic modifications, including glycosylation, glycation, hydroxylation and the like.

Isolated or purified antibodies to the peptide fragments described herein may be readily prepared by one skilled in the art given the disclosure provided herein and can be used for assaying purposes, therapeutic purposes or for diagnostic purposes.

A peptide fragment of the invention or antigenic portion thereof can be used to prepare antibodies specific for the peptide fragment. Antibodies can be prepared which bind a distinct epitope of the peptide fragment or can recognize an epitope created by a combination of peptide fragments, either in overlapping regions or to secondary structure elements of, for example dimmers or trimers of peptide fragments. These antibodies can be used to inhibit the activity of the peptide, may be useful for assays designed to identify inhibitors of the generation of said peptide fragments, or may also be used for diagnostic purposes to monitor disease state and disease progression in a variety of tissue samples.

Conventional methods can be used to prepare the antibodies. For example, by using a peptide of the invention, polyclonal antisera or monoclonal antibodies can be made using standard methods. This invention also contemplates chimeric antibody molecules, made by methods known to those skilled in the art.

The antibodies may be labelled with a detectable marker including various enzymes, fluorescent materials, luminescent materials and radioactive materials as is known to those skilled in the art.

Antibodies reactive against naturally occurring EPCA and fragments thereof (e.g., enzyme conjugates or labelled derivatives) may be used to detect EPCA, including the peptide sequence in various samples, such as tissue or body fluid samples. For example, they may be used in any known immunoassays and immunological methods that rely on the binding interaction between an antigenic determinant of a protein of the invention and the antibodies. Examples of such assays are radioimmunoassays, Western immunoblotting, enzyme immunoassays (e.g. ELISA), immunofluorescence, immunoprecipitation, latex agglutination, and immunohistochemical tests. Thus, the antibodies may be used to identify or quantify the amount of EPCA in a sample and thus may be used as a diagnostic indicator of disease state.

A sample may be tested for the presence or absence of EPCA by contacting the sample with an antibody specific for an epitope of the peptide fragment, which antibody is capable of being detected after it becomes bound to EPCA in the sample, and assaying for antibody bound to EPCA in the sample, or unreacted antibody.

In the method of the immunoassay, a predetermined amount of a sample or concentrated sample is mixed with antibody or labelled antibody. The amount of antibody used in the method is dependent upon the labelling agent chosen. The amount of EPCA bound to antibody or labelled antibody may then be detected by methods known to those skilled in the art. The sample or antibody may be insolubilized, for example, the sample or antibody can be reacted using known methods with a suitable carrier. Examples of suitable carriers are Sepharose or agarose beads. When an insolubilized sample or antibody is used, EPCA bound to antibody or unreacted antibody is isolated by washing. For example, when the sample is blotted onto a nitrocellulose membrane, the antibody bound to EPCA is separated from the unreacted antibody by washing with a buffer, for example, phosphate buffered saline (PBS) with bovine serum albumin (BSA).

When labelled antibody is used, the presence of EPCA can be determined by measuring the amount of labelled antibody bound in the sample. The appropriate method of measuring the labelled material is dependent upon the labelling agent.

When unlabelled antibody is used in a method of the invention, the presence of EPCA can be determined by measuring the amount of antibody bound to one or more EPCA molecules using substances that interact specifically with the antibody to cause agglutination or precipitation. In particular, labelled antibody against an antibody specific for EPCA, can be added to the reaction mixture. The antibody against an antibody specific for a peptide of the invention can be prepared and labelled by conventional procedures known in the art which have been described herein. The antibody against an antibody specific for a EPCA may be a species specific anti-immunoglobulin antibody or monoclonal antibody, for example, goat anti-rabbit antibody may be used to detect rabbit antibody specific for a peptide of the invention.

The methods of the invention may be performed on any related tissue or body fluid sample, preferably a prostate tissue and more preferably, a prostate biopsy tissue. Alternatively, the methods of the invention can be performed on a body fluid sample selected from the group consisting of blood, plasma, serum, fecal matter, urine, semen, seminal fluid or plasma.

Preferred according to the present invention is EPCA, including fragments thereof, and conservatively substituted variants thereof. Minor modifications of the EPCA primary amino acid sequence may result in proteins which have substantially equivalent activity as compared to the EPCA polypeptide described herein. Such modifications may be deliberate, as by site-directed mutagenesis, or may be spontaneous, and can include deletion of non-essential amino acids. All of the EPCA polypeptides produced by these modifications are included herein as long as the biological or immunological activity of the native EPCA still exists. Further, deletion of one or more amino acids can also result in a modification of the structure of the resultant molecule without significantly altering its biological activity. This can lead to the development of a smaller active molecule which would have broader utility.

The term "conservative substitution" as used herein denotes the replacement of an amino acid residue by a structurally similar residue. Examples of conservative substitutions include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like.

EPCA and fragments thereof can be synthesized by the well known solid phase peptide synthesis methods described, for example, by Merrifield, *J. Am. Chem. Soc.* 85:2149 (1962), and by Stewart and Young, SOLID PHASE PEPTIDES SYNTHESIS 27-62 (Freeman Publ., 1969).

Polyclonal and monoclonal antibodies of the invention are immunoreactive with EPCA or immunogenic fragments of EPCA. If desired, polyclonal antibodies can be further purified, for example, by binding to and elution from a matrix to which EPCA polypeptide is bound or by utilizing non-EPCA proteins, preferably including NMPs, to selectively remove non-specific antibodies. Antibodies which consist essentially of pooled monoclonal antibodies with different epitopic specificities, as well as distinct monoclonal antibody preparations, are provided.

The term "antibody" includes any synthetic or genetically engineered protein that is functionally capable of binding an epitopic determinant of EPCA. It also refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An "antibody fragment" is a portion of an antibody such as F(ab')$_2$, F(ab)$_2$, Fab', Fab, Fv, scFv (single chain Fv) and the like. Regardless of structure, an antibody fragment binds with the same EPCA antigen that is recognized by the intact antibody.

The term "antibody fragment" also includes any synthetic or genetically engineered protein that acts like an antibody by binding to a specific EPCA antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region. The Fv fragments may be constructed in different ways as to yield multivalent and/or multispecific binding forms. In the former case of multivalent, they react with more than one binding site against the specific epitope, whereas with multispecific forms, more than one epitope (either of the antigen or even against the specific antigen and a different antigen) is bound.

As used herein, the term "antibody component" includes both an entire antibody, a fusion protein, and fragments of any of them.

A "chimeric antibody" is a recombinant protein that contains the variable domains of both the heavy and light antibody chains, including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A "humanized antibody" is a recombinant protein in which the CDRs from an antibody from one species, e.g., a rodent antibody, is transferred from the heavy and light variable chains of the rodent antibody into human heavy and light variable domains. The constant domains of the antibody molecule are derived from those of a human antibody.

A "human antibody" is an antibody obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g., Johnson and Chiswell, *Current Opinion in Structural Biol.* 3:5564-571 (1993).

A preferred method for the identification and isolation of antibody binding domains which exhibit binding with EPCA is the bacteriophage X vector system. This vector system has been used to express a combinatorial library of Fab fragments from the mouse antibody repertoire in *Escherichia coli*, see Huse et al., *Science* 246:1275-81 (1989), and from the human antibody repertoire. Nullinax et al., *Proc. Natl. Acad. Sci. USA* 87:8095-99 (1990).

As used herein, the term "cell-proliferative disorder" denotes malignant as well as non-malignant (or benign) disorders of the prostate. This term further encompasses hyperplastic disorders of the prostate. The cells comprising these proliferative disorders often appear morphologically and genotypically to differ from the surrounding normal tissue. As noted above, cell-proliferative disorders may be associated, for example, with expression or absence of expression of EPCA. Expression of EPCA at an inappropriate time during the cell cycle or in an incorrect cell type may result in a cell-proliferative disorder. The EPCA-encoding polynucleotide in the form of an antisense polynucleotide may be useful in treating hyperplasia and malignancies of the prostate. When the cell-proliferative disorder is associated with EPCA expression, an antisense EPCA polynucleotide sequence or EPCA binding antibody can be introduced into the prostate cells to block the expression and/or function of EPCA. Alternatively, when the cell proliferative disorder is associated with under-expression or expression of a mutant EPCA polypeptide, a polynucleotide sequence encoding the missing or under-expressed EPCA can be introduced into the cell.

For purposes of the invention, an antibody or nucleic acid probe specific for an EPCA may be used to detect the presence of the EPCA polypeptide (in the case of an antibody probe) or polynucleotide (in the case of the nucleic acid probe) in biological fluids or tissues suspected of containing the EPCA. Oligonucleotide primers based on any coding sequence region in the EPCA sequence are useful for amplifying DNA or RNA, for example by PCR. The term "amplification" as used herein, relates to the production of additional copies of a nucleic acid sequence. Amplification is generally carried out using polymerase chain reaction (PCR) technologies that are well known in the art. (See, e.g., Dieffenbach, C. W. and G. S. Dveksler (1995), PCR Primer, a Laboratory Manual, Cold Spring Harbor Press, Plainview, N.Y., pp. 1-5). Any specimen containing a detectable amount of EPCA antigen can be used. A preferred sample of this invention is tissue taken from the prostate. Alternatively, biological fluids which may contain cells of the prostate may be used.

The term "subject" as used herein refers to mammals, preferably humans.

Another technique that may also result in greater sensitivity consists of coupling the probe to low molecular weight haptens. These haptens can then be specifically detected by means of a second reaction. For example, it is common to use such haptens as biotin, which reacts with avidin, or dinitrophenol, pyridoxal, and fluorescein, which can react with specific anti-hapten antibodies.

The method for detecting a cell expressing EPCA or a cell-proliferative disorder associated with EPCA, described above, can be utilized for detection of residual prostate cancer or other malignancies or benign hyperplasia conditions in a subject in a state of clinical remission. Additionally, the method for detecting EPCA polypeptide in cells is useful for detecting a cell-proliferative disorder by identifying cells expressing specific EPCA in comparison with other NMPs expressed in normal cells. Using the method of the invention, EPCA expression can be identified in a cell and the appropriate course of treatment can be employed (e.g., EPCA-encoding or antisense gene therapy, as well as conventional methods including, for example, surgical excision, radiation therapy and chemotherapy). Since the expression pattern of the EPCA of the invention varies with the stage of malignancy of a cell, a sample of prostate tissue can be screened with a panel of EPCA-specific reagents, e.g., nucleic acid probes or antibodies to EPCA or fragments thereof, to detect EPCA expression and diagnose the stage of malignancy of the cell.

Monoclonal antibodies of the invention are suitable for use in immunoassays in which they can be utilized in liquid phase or bound to a solid phase carrier. In addition, the monoclonal antibodies in these immunoassays can be detectably labeled in various ways. Examples of types of immunoassays that can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be performed utilizing immunoassays that are run in either the forward, reverse, or simultaneous modes, including immunohistochemical assays on physiological samples. Alternatively, the antibody of the invention can be used to detect EPCA present in electrophoretically dispersed gel protocols such as Western blots and two-dimensional gels.

Monoclonal antibodies of the invention can be bound to many different carriers and used to detect the presence of EPCA. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention.

In performing the assays it may be desirable to include certain "blockers" in the incubation medium (usually added with the labeled soluble antibody). The "blockers" are added to ensure that non-specific proteins, proteases, or anti-heterophilic immunoglobulins to anti-EPCA immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

It has been found that a number of nonrelevant (i.e., non-specific) antibodies of the same class or subclass (isotype) as those used in the assays (e.g., IgG1, IgG2a, IgM, etc.) can be used as "blockers." The "blockers" are used at a level high enough to maintain the proper sensitivity yet inhibit any unwanted interference by mutually occurring cross reactive proteins in the specimen (normally 1-100 µg/µl).

In this description, the term "epitope" denotes any determinant capable of specific interaction with the monoclonal antibodies of the invention. Epitopic determinants usually comprise chemically active surface groupings of molecules such as amino acids or sugar side chains and usually have specific three dimensional structural characteristics, as well as specific charge characteristics.

In using the monoclonal antibodies of the invention for in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the EPCA antigen for which the monoclonal antibody is specific.

The dosage of detectably labeled monoclonal antibody for in vivo diagnosis will vary depending on such factors as age, sex, and extent of disease of the individual. The dosage of monoclonal antibody can vary from about 0.001 mg/m$^2$, to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tumor burden, and other factors.

For in vivo diagnostic imaging, the type of detection instrument available is a major factor in selecting a given radioisotope. The radioisotope chosen must have a type of decay that is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140-250 keV range, which may be readily detected by conventional gamma cameras.

For in vivo diagnosis, radioisotopes may be bound to immunoglobulin either directly or indirectly by using an intermediate functional group. Intermediate functional groups that often are used to bind radioisotopes that exist as metallic ions to immunoglobulins are the bifunctional chelating agents such as diethylene-triaminepentacetic acid (DTPA) and ethylenediaminetetraacetic acid (EDTA) and similar molecules. Typical examples of radioisotopes which can be bound to the monoclonal antibodies of the invention are $^{111}$In, $^{97}$Ru, $^{67}$Ga, Ga, $^{72}$As, $^{89}$Zr, and $^{201}$Tl.

Monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and para-magnetic isotopes for MRI. Elements that are particularly useful in such techniques include $^{57}$Gd, $^{55}$Mn, $^{162}$Dy, $^{52}$Cr, and $^{56}$Fe.

Monoclonal antibodies of the invention can be used to monitor the course of amelioration of an EPCA-associated cell-proliferative disorder. Thus, by measuring the increase or decrease in the number of cells expressing EPCA or changes in EPCA (or fragments thereof) present in various body fluids, such as ejaculate, serum, plasma or urine, it would be possible to determine whether a particular therapeutic regimen aimed at ameliorating the disorder is effective.

Monoclonal antibodies of the invention can also be used, alone or in combination with effector cells (Douillard et al., *Hybridoma* 5 (S 1):S139 (1986)), for immunotherapy in an animal having a cell proliferative disorder that expresses one or more polypeptides with epitopes reactive with monoclonal antibodies of the invention.

Methods that directly compare the qualitative and quantitative protein content of tumor and normal cells are known in the art. These methods include immunoassays, one-dimensional and two-dimensional gel electrophoresis characterization, western blotting, matrix assisted laser desorption/time of flight (MALDI/TOF) mass spectrometry, liquid chromatography quadruple ion trap electrospray (LCQ-MS) and surface enhanced laser desorption ionization/time of flight (SELDI/TOF) mass spectrometry. These methods coupled with the laser capture microdissection method of Liotta et al. (WO 00/49410) can determine the protein characteristics of tumor cells, such as binding ability and amino acid sequence.

The present invention contemplates using the above-mentioned methods to compare the protein of the present invention in normal and cancerous prostate tumor cells. EPCA, as a target protein, can be used either alone or in combination with a ligand, such as a monoclonal antibody. For example, SELDI can be used in combination with a time-of-flight mass spectrometer (TOF) to provide a means to rapidly analyze EPCA or its peptide fragments retained on a chip (Hutchens and Yip, *Rapid Commun. Mass Spectrom.* 7:576-580, 1993). SELDI/TOF can be applied to ligand-protein interaction analysis by covalently binding the target protein on the chip and using mass spectroscopy to analyze the small molecules that bind to the target protein (Worrall et al. *Anal Biochem.* 70:750-756, 1998). In a typical experiment, an EPCA target to be analyzed is recombinantly expressed, optionally with a tag, such as poly-histidine, to facilitate purification and handling. The purified protein is bound to the SELDI chip either by utilizing the poly-histidine tag or by other interaction such as ion exchange or hydrophobic interaction. The chip thus prepared is then exposed to a candidate compound via, for example, a delivery system able to pipet the ligands in a sequential manner (autosampler). The chip is then washed in buffers of increasing stringency, for example a series of buffer solutions containing incrementally increasing ionic strength. After each wash, the bound material is analyzed by SELDI-TOF. Compounds that specifically bind the target are identified by elution in high stringency washes. For additional background on SELDI-TOF, see Zhang et al., *Science* 298: 995-1000, 20002 and Hutchens and Yip, U.S. Pat. Nos. 5,894,063, 5,719,060, and 6,027,942. The entire contents of the above-mentioned references are hereby incorporated by reference in their entirety.

The immunological processes of a human subject may produce auto-antibodies directed to the protein of the present invention (EPCA), as a result of prostate cancer. These antibodies, directed to a self-derived EPCA protein, would be an auto-antibodies by definition. As such, EPCA auto-antibodies can be measured in body fluids or tissues by immunological in vitro diagnostic methods wherein the EPCA protein or antigenic fragments thereof can be used as target substrates. The detection of EPCA auto-antibodies may correlate with the pathological state of prostate cancer and, therefore, would be useful for diagnostic purposes.

Auto-antibodies reactive with EPCA can be measured by a variety of immunoassay methods. For a review of immunological and immunoassay procedures in general, see Basic and Clinical Immunology, 7th Edition, D. Stites and A. Terr (ed.), 1991; "Practice and Theory of Enzyme Immunoassays," P. Tijssen, Laboratory Techniques in Biochemistry and Molecular Biology, Elsevier Science Publishers, B. V., Amsterdam (1985); and Harlow and Lane, Antibodies, A Laboratory Manual. The entire contents of these references are incorporated herein by reference.

When used for immunotherapy, the monoclonal antibodies of the invention may be unlabeled or attached to a therapeutic agent. These agents can be coupled either directly or indirectly to the monoclonal antibodies of the invention. One example of indirect coupling is by use of a spacer moiety. These spacer moieties, in turn, can be either insoluble or soluble (Diener et al., *Science* 231:148 (1986)), and can be selected to enable drug release from the monoclonal antibody molecule at the target site. Examples of therapeutic agents that can be coupled to the monoclonal antibodies of the invention for immunotherapy are drugs, radioisotopes, lectins, and toxins.

Drugs that can be conjugated to the monoclonal antibodies of the invention include non-proteinaceous as well as proteinaceous drugs. The terms "non-proteinaceous drugs" encompasses compounds that are classically referred to as drugs, for example, mitomycin C, daunorubicin, vinblastine, and others used to treat cancer.

Proteinaceous drugs with which the monoclonal antibodies of the invention can be joined include immunomodulators and other biological response modifiers. The term "biological response modifiers" encompasses substances that are involved in modifying the immune response in such manner as to enhance the destruction of EPCA-associated tumor for which the monoclonal antibodies of the invention are specific. Examples of immune response modifiers include such compounds as lymphokines. Lymphokines include tumor necrosis factor, the interleukins, lymphotoxin, macrophage activating factor, migration inhibition factor, colony stimulating factor, and interferon. Interferons with which the monoclonal antibodies of the invention can be labeled include alpha-interferon, beta-interferon and gamma-interferon and their subtypes.

In using radioisotopically conjugated monoclonal antibodies of the invention for immunotherapy, certain isotopes may be more preferable than others, depending on such factors as tumor cell distribution as well as isotope stability and emission. If desired, the tumor cell distribution can be evaluated by the in vivo diagnostic techniques described above. Depending on the cell proliferative disease some emitters may be preferable to others. In general, alpha and beta particle-emitting radioisotopes are preferred in immunotherapy. For example, if an animal has solid tumor foci a high energy beta emitter capable of penetrating several millimeters of tissue, such as $^{90}$Y, may be preferable. On the other hand, if the cell proliferative disorder consists of simple target cells, as in the case of leukemia, a short range, high energy alpha emitter, such as Bi, may be preferable. Examples of radioisotopes that can be bound to the monoclonal antibodies of the invention for therapeutic purposes are radioisotopes of $^{125}$I, $^{131}$I, $^{90}$Y, $^{67}$Cu, $^{212}$Bi, $^{211}$At, $^{212}$Pb, $^{47}$Sc, $^{109}$Pd, $^{65}$Zn, and $^{188}$Re.

Lectins are proteins, usually isolated from plant material, that bind to specific sugar moieties. Many lectins are also able to agglutinate cells and stimulate lymphocytes. Ricin is a toxic lectin which has been used immunotherapeutically. The alpha-peptide chain of ricin, which is responsible for toxicity, may be bound to the antibody of the invention to enable site specific delivery of the toxic effect.

Toxins are poisonous substances produced by plants, animals, or microorganisms, that, in sufficient dose, may often be lethal. Diphtheria toxin is a substance produced by *Corynebacterium diphtheria* which can be used therapeutically. This toxin consists of an alpha and beta subunit which under proper conditions can be separated. The toxic A component can be bound to an antibody and used for site specific delivery to an EPCA-bearing cell.

The monoclonal antibodies of the invention can be used in combination with alpha-interferon. This treatment modality enhances monoclonal antibody targeting of carcinomas by increasing the expression of monoclonal antibody reactive antigen by the carcinoma cells. Greiner et al., *Science* 235: 895 (1987). Alternatively, the monoclonal antibody of the invention can be used, for example, in combination with gamma-interferon to thereby activate and increase the expression of Fc receptors by effector cells which, in turn, results in an enhanced binding of the monoclonal antibody to the effector cell and killing of target tumor cells.

It also is possible to utilize liposomes with the monoclonal antibodies of the invention in their membrane to specifically deliver the liposome to the tumor expressing EPCA. These liposomes can be produced such that they contain, in addition to the monoclonal antibody, such therapeutic agents as those described above which would then be released at the tumor site. Wolff et al., *Biochemical et Biophysical Acta* 802:259 (1984).

Dosage ranges for the administration of monoclonal antibodies of the invention are those large enough to produce the desired effect in which the symptoms of the malignant disease are ameliorated. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when the monoclonal antibodies of the invention are administered conjugated with therapeutic agents, lower dosages, comparable to those used for in vivo diagnostic imaging, can be used.

Monoclonal antibodies of the invention can be administered parenterally by injection or by gradual perfusion over time. The monoclonal antibodies can be administered intravenously, intraperitoneally, intramuscularly, subcutaneously, intracavity, or transdermally, alone or in combination with effector cells.

Transformation of a host cell with recombinant DNA may be performed by conventional techniques known in the art. Where the host is prokaryotic, such as *E. coli*, competent cells which are capable of DNA uptake can be prepared from cells harvested after the exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with DNA sequences encoding the NMPs of the invention, and a second foreign DNA molecule encoding a selectable phenotype, such as the herpes simplex thymidine kinase gene. Another method is to use a eukaryotic viral vector, such as simian virus 40 (5V40) or bovine papilloma virus, to transiently infect or transform eukaryotic cells and express the protein. Eukaryotic Viral Vectors, Gluzman (ed.), Cold Spring Harbor Laboratory, 1982.

Isolation and purification of EPCA or fragments thereof expressed by a transformed host may be carried out by conventional means including preparative chromatography and immunological separations involving monoclonal or polyclonal antibodies. Antibodies provided in the present invention are immuno-reactive with EPCA polypeptide or fragments thereof.

The present invention also provides a method for treating a subject with an EPCA-associated cell-proliferative disorder using an EPCA nucleotide sequence or portion thereof. An EPCA nucleotide sequence that may encode a suppressor polypeptide may be under-expressed as compared to expression in a normal cell, therefore it is possible to design appropriate therapeutic or diagnostic techniques directed to this sequence. Thus, where a cell-proliferative disorder is associated with the expression of EPCA, which is associated with malignancy, nucleic acid sequences that interfere with EPCA expression at the translational level can be used. This approach utilizes, for example, antisense nucleic acid and ribozymes to block translation of a specific EPCA mRNA, either by masking that mRNA with an antisense nucleic acid or by cleaving it with a ribozyme. In cases when a cell proliferative disorder or abnormal cell phenotype is associated with the under expression of EPCA suppressor for example, nucleic acid sequences encoding UMP (sense) could be administered to the subject with the disorder.

Antisense nucleic acids are DNA or RNA molecules that are complementary to at least a portion of a specific mRNA molecule. Weintaub, *Scientific American* 262: 40 (1990). In the cell, the antisense nucleic acids hybridize to the corresponding mRNA, forming a double-stranded molecule. The antisense nucleic acids interfere with the translation of the mRNA since the cell will not translate a mRNA that is double-stranded. Antisense oligomers of about 15 nucleotides are preferred, since they are easily synthesized and are less likely to be expressed than larger molecules when introduced into the target NMP-producing dell.

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it. Cech, *J. Amer. Med. Assn.* 260:3030 (1988). A major advantage of this approach is that, because they are sequence-specific, only in RNAs with particular sequences are inactivated.

There are two basic types of ribozymes namely, tetrahymena-type (Hasselhoff, *Nature* 334:585 (1988)) and "hammerhead"-type. Tetrahymena-type ribozymes recognize sequences which are four bases in length, while "hammerhead"-type ribozymes recognize base sequences 11-18 bases in length. The longer the recognition sequence, the greater the likelihood that that sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous."

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity." Two or more amino acid sequences likewise can be compared by determining their "percent identity." The percent identity of two sequences, whether nucleic acid or peptide sequences, is the number of exact matches between two aligned sequences divided by the length of the shorter sequences and multiplied by 100. An approximate alignment for nucleic acid sequences is provided by the local homology algorithm of Smith and Waterman, *Adv. Appl. Math.* 2:482-489 (1981). This algorithm can be extended to use with peptide sequences using the scoring matrix developed by Dayhoff, Atlas of Protein Sequences and Structure, M. O. Dayhoff (ed), 5 Suppl. 3:353-358, National Biomedical Research Foundation, Washington, D.C., USA, and normalized by Gribskov (*Nucl. Acids Res.* 14(6):6745-6763 (1986). An implementation of this algorithm for nucleic acid and peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

"Hybridization," as the term is used herein, refers to any process by which a strand of nucleic acid binds with a complementary strand through base pairing. As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand to any DNA-like or RNA-like material. In this context, "fragments" preferably refers to those nucleic acid sequences that are greater than about 60 nucleotides in length, and most preferably are at least about 100 nucleotides, at least about 1000 nucleotides, or at least about 10,000 nucleotides in length.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

It is contemplated that polynucleotides will be considered to hybridize to the sequences provided herein if there is at least 50%, preferably at least 70%, and more preferably at least 90% identity between the polynucleotide and the sequence. The degree of sequence identity between two nucleic acid molecules greatly affects the efficiency and strength of hybridization events between such molecules. A partially identical nucleic acid sequence is one that will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, in situ hybridization, or the like, see Sambrook, et al., Molecular Cloning: A Laboratory Manual, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. In one embodiment of the present invention, a nucleic acid molecule is capable of hybridizing selectively to a target sequence under moderately stringent hybridization conditions. In the context of the present invention, moderately stringent hybridization conditions allow detection of a target nucleic acid sequence of at least 14 nucleotides in length having at least approximately 70% sequence identity with the sequence of the selected nucleic acid probe. In another embodiment, such selective hybridization is performed under stringent hybridization conditions. Stringent hybridization conditions allow detection of target nucleic acid sequences of at least 14 nucleotides in length having a sequence identity of greater than 90% with the sequence of the selected nucleic acid probe. Hybridization conditions useful for probe/target hybridization where the probe and target have a specific degree of sequence identity, can be determined as is known in the art (see, for example, Nucleic Acid Hybridization: A Practical Approach, B. D. Hames and S. J. Higgins (eds.), Oxford; Washington, D.C.; IRL Press, 1985). Hybrid molecules can be formed, for example, on a solid support, in solution, and in tissue sections. The formation of hybrids can be monitored by inclusion of a reporter molecule, typically, in the probe. Such reporter molecules, or detectable elements include, but are not limited to, radioactive elements, fluorescent markers, and molecules to which an enzyme-conjugated ligand can bind.

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is well within the skill of the routineer in the art (see, for example, Sambrook, et al., Molecular Cloning: A Laboratory Manual, Second Edition, (1989) Cold Spring Harbor, N.Y.).

Probes constructed according to the polynucleotide sequences of the present invention can be used in various assay methods to provide various types of analysis. For example, such probes can be used in fluorescent in situ hybridization (FISH) technology to perform chromosomal analysis, and used to identify prostate cancer-specific structural alterations in the chromosomes, such as deletions or translocations that are visible from chromosome spreads or detectable using PCR-generated and/or allele specific oligonucleotides probes, allele specific amplification or by direct sequencing. Probes also can be labeled with radioisotopes, directly- or indirectly-detectable haptens, or fluorescent molecules, and utilized for in situ hybridization studies to evaluate the mRNA expression of the gene comprising the polynucleotide in tissue specimens or cells.

The sequences provided herein may be used to produce probes which can be used in assays for the detection of nucleic acids in test samples. The probes may be designed from conserved nucleotide regions of the polynucleotides of interest or from non-conserved nucleotide regions of the polynucleotide of interest. The design of such probes for optimization in assays is within the skill of the routineer. Generally, nucleic acid probes are developed from non-conserved or unique regions when maximum specificity is desired, and nucleic acid probes are developed from conserved regions when assaying for nucleotide regions that are closely related to, for example, different members of a multigene family or in related species like mouse and man.

The polymerase chain reaction (PCR) is a technique for amplifying a desired nucleic acid sequence (target) contained in a nucleic acid or mixture thereof. In PCR, a pair of primers is employed in excess to hybridize to the complementary strands of the target nucleic acid. The primers are each extended by a polymerase using the target nucleic acid as a template. The extension products become target sequences themselves, following dissociation from the original target strand. New primers then are hybridized and extended by a polymerase, and the cycle is repeated to geometrically increase the number of target sequence molecules. PCR is disclosed in U.S. Pat. Nos. 4,683,195 and 4,683,202, which are incorporated herein by reference.

Suitable hybridization formats are well known to those of skill in the art and include, but are not limited to, variations of Southern Blots, in situ hybridization and quantitative amplification methods such as quantitative PCR (see, e.g., Sambrook, Molecular Cloning—A Laboratory Manual, Cold Spring Harbor Laboratory, Cold Spring Harbor, N.Y., (1989), Kallioniemi et al., Proc. Natl. Acad. Sci. USA, 89:5321-5325 (1992), and PCR Protocols, A Guide to Methods and Applications, Innis et al., Academic Press, Inc. N.Y., (1990)).

Generally, in situ hybridization comprises the following major steps: (1) fixation of tissue or biological structure to analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and their conditions for use vary depending on the particular application.

The FISH protocol employing the claimed polynucleotide to diagnose prostate cancer can be found in Klijanienko, J. et al., Cancer 87:312-318 (1999) and Wu, S.-Q. et al., Int. J. Oncol. 19:1143-1147 (2001).

The present invention also provides gene therapy for the treatment of cell proliferative disorders which are mediated by EPCA. Such therapy requires introduction of the appropriate EPCA polynucleotide sequence (antisense or encoding strand) into cells of subjects having the proliferative disorder. Delivery of antisense EPCA polynucleotides can be achieved using a recombinant expression vector such as a chimeric virus or a liposome. Disorders associated with over-expression of EPCA or expression of a cancer-associated EPCA can be treated using gene therapy with the encoding or antisense nucleotide sequences, respectively.

Various viral vectors that can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), inurine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting an EPCA sequence of interest into the viral vector along with another gene that encodes the ligand for a receptor on a specific target cell, for example, the vector is rendered target specific. Retroviral vectors can be made target-specific by inserting, for example, a polynucleotide encoding a sugar, a glycolipid, or a protein. Preferred targeting is accomplished by using an antibody to target the retroviral vector.

Since recombinant retroviruses are defective in one or more genes, they require assistance to produce infectious vector particles. Helper cell lines that have deletions of the packaging signal include, but are not limited to W2, PA317 and PA12, for example. These cell lines produce empty virions, because no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env by conventional calcium phosphate transfection. These cells are then transfected with the vector plasmid containing the genes of interest. The resulting cells release the retroviral vector into the culture medium.

Other targeted delivery systems for EPCA antisense polynucleotides include macromolecule complexes, nanocapsules, microspheres, beads, and lipid-based systems including oil-in-water emulsions, micelles, mixed micelles, and liposomes. Liposomes are artificial membrane vesicles which are useful as delivery vehicles in vitro and in vivo. It has been shown that large unilamellar vesicles (ULV), which range in size from 0.2-4.0 pm can encapsulate a substantial percentage of an aqueous buffer containing large macromolecules. RNA, DNA and intact virions can be encapsulated within the aqueous interior and be delivered to cells in a biologically active form. Fraley et al., Trends Biochem. Sci. 6: 77 (1981).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidyiserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific and organelle-specific. Mechanistic targeting can be distinguished based upon whether it is passive or active. Passive targeting utilizes the natural tendency of liposomes to distribute to cells of the reticulo-endothelial system (RES) in organs that contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor.

In general, surface membrane proteins that bind to specific effector molecules are referred to as receptors. In the present invention, antibodies of the invention are preferred receptors. Antibodies can be used to target liposomes to EPCA-specific cell-surface ligands. Preferably, the target tissue is prostate tissue. A number of procedures can be used to attach either polyclonal or monoclonal antibodies covalently to a liposome bilayer. Antibody-targeted liposomes can include monoclonal or polyclonal antibodies or fragments thereof such as Fab, or F(ab')$_2$, as long as they bind efficiently to an the antigenic epitope on the target cells.

The present invention also provides an immunotherapeutic method for treating a subject with an EPCA-associated cell-proliferative disorder using dendritic cell therapy. Dendritic cells are antigen-presenting cells. In one aspect of the invention, EPCA, used as the target antigen, is combined with the patient's own dendritic cells and reinfused back into the patient to stimulate an immune response. The introduction of a therapeutic vaccine such as an EPCA vaccine may result to the lowering of EPCA levels and eventually the shrinkage of the prostate tumor. Such immunotherapeutic methods have been used and known in the art. An example of such use in prostate cancer treatment is the application of the Provenge B vaccine, manufactured by Dendreon Corporation, in prostate cancer patients. This vaccine is currently in Phase III clinical trials for the treatment of advanced prostate cancer and earlier stage prostate cancer. For more information on this vaccine, please consult the Dendreon Corporation at 3005 First Avenue Seattle, Wa. 98121 (dendreon.com). For background information on dendritic cell therapy, please refer to WO 01/88105; WO 00/28000; WO 99/63050; WO 97/32992; and U.S. Pat. Nos. 6,340,461; 6,184,436; 6,130,316; 6,100,443; 6,436,411; and 6,077,519. The entire contents of the above-mentioned references are hereby incorporated by reference in their entirety.

Preparations for parenteral administration include sterile aqueous or nonaqueous solutions, suspensions, and emulsions. Examples of non aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such an those based on Ringer's dextrose), and the like. Preservatives and other additives may also be present such as, for example, antimicrobials, anti-oxidants, chelating agents and inert gases and the like.

The invention also relates to a method for preparing a medicament or pharmaceutical composition comprising the EPCA polynucleotides or the monoclonal antibodies of the invention, the medicament being used for prostate therapy.

The embodiments of the invention may be further illustrated through examples that show aspects of the invention in detail. These examples illustrate specific elements of the invention and are not to be construed as limiting the invention's scope.

EXAMPLES

Isolation and Sequencing of Rat Nuclear Matrix Proteins

A rat model system was utilized to identify targets, which were then investigated in human samples.

The G, AT2.1 and MLL sublines of the Dunning R3327 rat prostate adenocarcinoma cell line were cultured in RPMI 1640 containing 10% fetal bovine serum, 250 nM dexamethasone, penicillin-G and streptomycin both at 100 units/ml. The cells were then harvested and fractionated to isolate nuclear matrix proteins, as described below.

The Dunning R3327 AT2.1 rat prostate tumors were transplanted subcutaneously into male Copenhagen rats and harvested when the tumor weights reached 34 grams. Normal rat dorsal prostates were obtained from mature intact male Sprague-Dawley rats (300-350 g) obtained from Charles River (Wilmington, Mass.). Tumor and tissue samples were fractionated to isolate nuclear matrix proteins as described below.

Normal and tumor prostate tissue samples were obtained from patients undergoing surgery for prostate cancer. Samples were only utilized that could clearly be identified by the pathologist as containing approximately pure populations of the stated cell type.

The nuclear matrix proteins were isolated from the prostate tissues, cells and tumors selected above according to the methods taught by Fey et al., *J. Cell Biol.* 98:1973-1984 (1988) and Getzenberg, et al., *Cancer Res.* 51:6514-6520 (1991).

The tissue pieces were minced into small (1 mm$^3$) pieces and homogenized with a Teflon pestle on ice with 0.5% Triton X-100 in a solution containing 2 mM vanadyl ribonucleoside (RNase inhibitor) to release the lipids and soluble proteins. Extracts were then filtered through a 350µ nylon mesh and extracted with 0.25M ammonium sulfate (containing 2 mM vanadyl ribonucleoside) to release the soluble cytoskeletal elements. DNase treatment at 25° C. was used to remove the soluble chromatin, followed by an optional RNase treatment. The isolation method was successfully performed both with and without an RNase treatment.

The remaining fractions contained intermediate filaments and nuclear matrix proteins. This fraction was then disassembled with 8 M urea. The insoluble components, which consisted principally of carbohydrates and extracellular matrix components, were pelleted. The urea was dialyzed out, and the intermediate filaments were allowed to reassemble and removed by centrifugation. The nuclear matrix proteins were then ethanol precipitated. All solutions contained freshly prepared 1 mM phenylmethylsulfonylfluoride (PMSF) to inhibit serine proteases, 0.3 µM aprotinin, 1 µM leupeptin and 1 µM pepstatin.

The nuclear matrix proteins were separated by the high resolution two-dimensional gel electrophoretic procedure. High resolution two-dimensional gel electrophoresis was carried out utilizing the Investigator 2-D gel system (Genomic Solutions, Chelmsford, Mass.). Briefly, one-dimensional isoelectric focusing was carried out for 18,000 V-h using 1-mm X 18-cm tube gels after 1.5 h of prefocusing. The tube gels were extruded and placed on top of 1-mm sodium dodecyl sulfate Duracryl (Genomic Solutions, Chelmsford, Mass.) high tensile strength polyacrylamide electrophoresis slab gels, and the gels were electrophoresed with 12° C. constant temperature regulation for approximately 5 hours. Gels were fixed with 50% methanol and 10% acetic acid. After thorough rinsing and rehydration, gels were treated with 5% glutaraldehyde and 5 mM dithiothreitol after buffering with 50 mM phosphate (pH 7.2). The gels were stained with silver stain (Accurate Chemical Co., Inc., Westbury, N.Y.) or transferred to PVDF (Immobilon, Millipore Corporation) as follows.

Fifty micrograms of nuclear matrix protein were loaded for each gel. Protein molecular weight standards were Silver Standards from Diversified Biotechnology (Newton Centre, Mass.). Isoelectric points were determined using carbamylated standards from Gallaro-Schlesiwger, Inc. (Carle Place, N.Y.) and Sigma Chemical Co. (St. Louis, Mo.). Multiple gels were run for each sample, and multiple samples run at different times. Only protein spots clearly and reproducibly observed in all the gels of a sample type were counted as actually representing the nuclear matrix components. The gels were analyzed using the BioImage Electrophoresis Analysis System (BioImage, Ann Arbor, Mich.) which matches protein spots between gels and databases the gels and protein spots. A unique combination of Chaps detergent and ampholyte was used to run these gels. Since tissues were used to isolate these nuclear matrix proteins, the resulting proteins are tissue nuclear matrix proteins which differ significantly from nuclear matrix proteins obtained from cell cultures.

A unique staining methodology was used to stain the high resolution two-dimensional gels. Utilizing a ZnCl negative staining technique, novel nuclear matrix proteins were identified without having to sequence them.

The inventor investigated how the nuclear matrix was altered in cancer cells and whether these matrix protein patterns could distinguish closely related sublines of the same Dunning tumor (14). The nuclear matrix proteins in several Dunning cell lines were examined and compared with the nuclear matrix protein composition of the dorsal prostate, the original tissue from which this tumor was derived. Using high-resolution two-dimensional gel electrophoresis, the NMPs of the Dunning cell lines were found to be significantly different from the rat dorsal prostate. A minimum of ten abundant proteins were identified as unique to the rat dorsal prostate when compared with the Dunning lines i.e., they were absent in the tumor cells. Similarly, there were several proteins, which were unique to the Dunning cell lines that were not found to be present in the dorsal prostate nuclear matrix. When the NMP patterns of the Dunning cell lines were compared with one another, they appeared relatively similar in protein composition. The metastatic AT-2 and MLL cell lines were alike in their protein composition of the relatively abundant proteins. However, these two cell lines did contain two proteins that were not found in the non-metastatic G cell line. Conversely, the nuclear matrix of the G cell line exhibited two proteins that were not present in the AT-2 or MLL cell lines.

The NMP patterns were compared for fresh prostate, benign prostatic hyperplasia (BPH), and prostate cancer from 21 men undergoing surgery for clinically localized prostate cancer or BPH. The NMP patterns were compared utilizing a high-resolution gel electrophoresis technique. Fourteen different proteins were identified by molecular weight and isoelectric point that were consistently present or absent among the various tissues. Sequence data was utilized that was generated for these proteins to produce anti-peptide antibodies.

One of these proteins, EPCA, was identified as being expressed in prostate cancer but not in other normal tissues or cancer types. In the examples herein, the expression of a novel nuclear matrix protein, EPCA, is reported in human prostate cancer. This protein is expressed throughout the prostate of individuals with prostate cancer and is useful to detect individuals with the disease even in biopsy samples that are morphologically negative. Furthermore, it can be used to detect the disease in these individuals more than two years prior to their being morphologically detected. These studies reveal the utility of anti-EPCA antibodies as an adjunct to pathologic examination of prostatic biopsies to detect prostate cancer earlier, and thus avoid or reduce the need for repeated biopsies in these individuals.

Protein Sequencing from Spots in 2-D Gels

To purify and concentrate sufficient quantities of EPCA for sequencing from spots in 2-D gels, protein was isolated according to an adaptation of a technique developed by Gavaert et al. (Gevaert, K., Rider, M., Puype, M., Van Damme, J., De Boeck, S., and Vandekerckhove, J. New strategies in high sensitivity characterization of proteins separated from 1-D or 2-D gels. In: Methods in Protein Structure Analysis, Atassi M. Z. and Appella, E. (eds). Plenum Press, New York. 15-26, 1995). The two-dimensional gels were negatively stained by incubating the gels in 0.2M imidazole for 15 minutes, washed several times with deionized water, and stained with warm 0.3M ZnCl. Deionized water was used to stop the staining and the protein gel spots were excised and frozen at −80° C. The spots were then thawed, pooled and mixed with 0.25% Coomassie blue stain (45% methanol/9% acetic acid) for 20 minutes. With constant agitation, the spots were destained with destaining solution (5% methanol/7.5% acetic acid) for 1 hour, washed with deionized water for 1 hour, and equilibrated in sample buffer (1% SDS/10% glycerol/50 mM DTT/12 mM Tris-HCl, pH 7.1) for 1 hour before loading into the acrylamide/agarose gel.

The spots were then concentrated on a mini-agarose/acrylamide gel. The construction of the mini-agarose gel consisted of two pre-warmed (60° C.) glass plates (10 cm×9 cm), separated by spacers 1 cm wide and 1.5 mm thick. A strip of Whatman 3 MM paper was inserted at the bottom to serve as a support for the lower agarose gel, preventing the gel from slippage during electrophoresis. The sample well was formed by a 2 cm wide×1.5 cm thick spacer set between two parallel spacers each 1 cm wide×1.5 cm thick inserted at the center of the glass plates and attached with adhesive tape at the top edge of the back plate.

The lower gel consisted of a 2 cm deep agarose gel (1.45% agarose in 0.36 M Tris-HCl pH 8.7/0.1% SDS). Once the agarose had set, it was overlaid with the polyacrylamide stacking gel (5.45% acrylamide/0.13% bisacrylamide/0.12 M Tris-HCl pH 6.8/0.1% SDS). When the stacking gel had set, the central spacer was removed, leaving a well 2 cm high, 2 cm wide and 1.5 mm thick. The mini concentration gel was then mounted on a small electrophoresis tank (BioRad, Hercules, Calif.), and the slot filled with the equilibrated 2-D gel spots. The remaining volume was filled with blank gel pieces.

The gels were run at 100 V, allowing the proteins to elute out of the combined gel pieces and into the acrylamide. At this time, the central spacer was re-inserted into the sample well until the dye front passed the two parallel 1 cm wide spacers. At that point, the central spacer was removed and electrophoresis continued until the dye front entered the agarose and reached the filter paper.

The agarose section of the gel was fixed in fresh 50% methanol/10% acetic acid shaking, at room temperature for 30 minutes. The gel was stained with 0.05% Coomassie blue stain (50% methanol/10% acetic acid) for 5 minutes and then destained in 5% methanol/7% acetic acid for 2 hours with constant agitation. The protein band was then excised in a minimal volume of agarose gel, transferred into an sterile tube, and sent for peptide sequencing (Department of Biochemistry, Michigan State University).

Isolation of sufficient quantities, as described above, permitted the internal peptide sequencing of this protein. Of the peptide sequences obtained, four resulted in sufficient amino acid sequence data to provide partial sequences. These four peptides along with the most significant matches obtained from BLAST analysis are outlined below:

VSNTPLPGVFTK (SEQ ID NO:1) (7 of 10): metastatic and invasion protein

TIGDNQK (SEQ ID NO:2) (6/6): matrix metalloproteinase 11

DAYPGQIS (SEQ ID NO:3) (7/8): MalK-like protein, (6/6) putative cuticle collagen, (6/6) yeast hypothetical protein, (6/6) trypsinogen 111 precursor DSGQGY (SEQ ID NO:4) (5/6): cellulose-binding beta-glucosidase Overall, while these data are suggestive of some regions that may be common to other proteins, it is believed that EPCA is, in fact, a novel and previously uncharacterized protein.

Antibody Production

A standard protocol was followed for the production of antibodies raised against the peptides sequenced above. Utilizing the peptide sequence derived from the corresponding spots from high-resolution two-dimensional gels, peptides were designed and polyclonal antibodies raised. These peptide sequences were chosen based upon the length of the sequence obtained. The peptides produced were modified slightly to include the addition of terminal cysteines for coupling purposes along with several amino acids for spacing to increase immunoreactivity. The sequences were verified through mass spectroscopy and conjugated to bovine serum albumin (BSA) utilizing the Pierce Inject Maleimide Activated Immunogen Kit (Pierce Chemical Co.) The resulting antigens were suspended in saline and emulsified by mixing with an equal volume of Freund's Adjuvant. Two New Zealand white rabbits (3-9 months old) were injected with the peptide into three to four subcutaneous dorsal sites four times over a three-month period. The animals were bled from the auricular artery and the serum collected from three production bleeds. Antibodies were produced by Cocalico Inc.

Immunohistochemical (IHC) Evaluation of Human Prostate Specimens

The immunohistochemical evaluation of EPCA staining in human prostate specimens was performed using two major tissue type sets. An initial screening of the EPCA antibody was performed using low-density tissue micro-arrays (TMA) prepared in-house. The TMA consisted of prostatic adenocarcinoma, metastatic carcinoma, high-grade PIN, normal tissue adjacent to the prostate cancers as well as benign prostatic hyperplasia. EPCA was identified in the foci of carcinoma, metastatic carcinoma, non-neoplastic tissue adjacent to tumor and high grade PIN and not in the foci of BPH. The study set was then constructed and consisted of two sets of cases. The first set, the non-diseased control sample set, consisted of prostate tissues obtained from donor prostatectomies. The donor prostatectomies were derived from organ donors, who had no evidence of prostatic disease. The second tissue set consisted of patients in whom radical prostatectomies were performed for adenocarcinoma of the prostate. These patients were selected on the basis of the presence of an earlier negative biopsy in our surgical pathology files. The tissue set, therefore, from these patients with prostatic adenocarcinoma consisted of an initial negative prostate biopsy, followed by a positive prostate biopsy and subsequent radical prostatectomy performed for the adenocarcinoma of the prostate.

The anti-EPCA antibody was used at a working dilution of 1:1000. This dilution was prepared using Dako antibody diluent with 0.05 M Tris-HCl buffer-containing 0.1% Tween, carrier proteins to reduce background and 15 mM sodium azide. The tissue samples, from both the donors and the patients with prostatic adenocarcinoma, had been routinely processed for histology, fixed overnight in 10% neutral buffered formalin and then paraffin embedded. The processing methodology was the same in both the donor prostatectomies and in the disease set. The paraffin blocks of the tissue specimens were cut at 34 micron thickness and mounted on positively charged slides. The slides were then dried overnight in a 37 degree centigrade incubator and then transferred to a 60-degree centigrade oven for 30 min. The slides were treated with Protease K (Dako) for 7 minutes. Immunohistochemical staining was performed on these slides using the Dako Autostainer and Dako's Rabbit Envision+ System which is based on the horseradish peroxidase (HRP) two-step IHC staining technique. In this system, an HRP labeled polymer is conjugated to the secondary antibodies. The labeled polymer does not contain avidin or biotin. This system is extremely sensitive and offers an enhanced signal generating system. The chromogen used was Di-Amino Benzidine (DAB) followed by enhancement with 1% $Cu_2SO_4$ for 5 minute and counterstaining with Hematoxylin. As a positive control, prostatic adenocarcinomas that are metastatic to the lymph nodes were used.

One observer evaluated all the slides. The staining intensities were graded on a scale of 0 (negative staining) to 3 (intense strong staining).

The control set selected consisted of donor prostatectomy specimens from patients with no documented history of prostatic disease (total of 29 cases). Subsequent evaluation documented high-grade prostatic intra-epithelial neoplasia (PIN) in one donor specimen while another donor had some, but not all changes, of high-grade PIN (best classified as intermediate grade PIN). These samples with their increased potential to contain prostate cancer were removed from further analysis. The control study set, therefore, consisted of 27 cases.

The disease set consisted of a total of 25 cases. The cases were selected based on the presence of a preceding negative biopsy, followed by a positive biopsy and subsequently a radical prostatectomy (RP) (see FIG. 1). The positive biopsy (+Bx) specimens showed a concordance with the prostatectomy Gleason score in 16 cases. There was a difference of 1 in the Gleason score in the remaining 9 cases, with an increase in the prostatectomy score in 8 cases and a decrease in the prostatectomy Gleason score in 1 case. The details of the characteristics of the disease set are presented in Table 1.

The Gleason distribution of the positive biopsies was as follows:

TABLE 1

| | Gleason Scoring | | | |
|---|---|---|---|---|
| | 5 | 6 | 7 | 8 |
| Positive Biopsy | 1 | 18 | 5 | 1 |
| Prostatectomy |  | 15 | 9 | 1 |

The racial characteristics were known in 13 patients, with 9 being Caucasians and 4 African American. The age distribution of the age at initial negative biopsy of the disease set and the control set (donor prostatectomy specimens) was as follows:

TABLE 2

| | Age Distribution | | | | | |
|---|---|---|---|---|---|---|
| | 10-20 yrs | 20-30 yrs | 30-40 yrs | 40-50 yrs | 50-60 yrs | 60-70 yrs |
| Donors | 6 | 10 | 4 | 5 | 3 | 1 |
| Age at Initial Bx | 0 | 0 | 0 | 1 | 8 | 16 |

The donor age distribution ranged from 17-63 years. The number of older donor samples were limited because of the accrual characteristics of the sample population. The age at initial biopsy (Bx) in the patients with prostatic adenocarcinoma ranged from 48-68 years. The donor set consisted of 7 cases with ages greater than 40 years.

Two tissue types were available to serve as the "non-diseased" (non-neoplastic) set. The first was the donor prostatectomies. The other was men with multiple negative biopsies (−Bx). The donors present a finite end point without any phenotypic evidence of disease, as established on pathology examination. The biologic situation in patients with negative biopsy can only be surmised, since the entire prostate was not evaluated. In addition, gene expression data generated by Yu, Y. P. et al. (*Nature Medicine*, in press) firmly establishes marked differences between donor prostates and prostate carcinoma and/or normal tissue adjacent to the prostate tumors (NAT). For these reasons, the donor prostatectomies were used as the negative case set.

The prostatectomy pathologic T stage was T2 in 24 cases and T3 in one case. This predominance of T2 could be a result of smaller tumor size, thus possibly accounting for the observed initial negative biopsy.

Margin positivity, however, was seen in 5 cases. These cases seemed to have smaller prostates, with weights ranging from 27-61 grams with an average of 41.4 grams. The overall tumor volume was variable in these cases, ranging from 5-20% (mean of 9%). The racial characteristics were known in 2 of the 5 cases with positive margins, with one being Caucasian and the other African American.

Human Studies with Anti-Peptide Antibodies

Anti-EPCA antibodies were produced as described and used for immunoblotting and IHC analysis. These antibodies detected the EPCA protein in the metastatic Dunning tumors, but not in non-metastatic G line or the normal rat prostate tissue. These results confirm that EPCA is a protein that is associated with tumors that have the ability to advance and metastasize.

Immunoblots of human prostatic samples revealed a surprising pattern of staining. They demonstrated that the EPCA protein is detected not only in the tumor samples but also in the normal adjacent areas of the prostate from these individuals. Expression of EPCA is not observed in the prostatic tissue obtained from organ donors without prostate cancer or in BPH samples. This analysis reveals that EPCA is a protein that is expressed in the tumor and normal adjacent areas of individuals with prostate cancer. The protein is not found in the prostates of organ donors. Therefore, EPCA may be prostate cancer specific in that it can detect "cancerous prostates" and separate them from the prostates of those without the disease.

Immunohistochemical (IHC) Analysis

The surprised finding that EPCA is expressed in the tumor and normal adjacent areas of individuals with prostate cancer but not in the prostates of individuals without the disease suggested to the inventor that EPCA could be used as a marker to detect individuals with prostate cancer when small tissue samples were examined. EPCA expression in tissue samples was examined by IHC in order to determine its intensity of expression and localization. The disease set consisted of a total of 25 cases. The cases were selected based on the presence of a preceding negative biopsy, followed by a positive biopsy and subsequent prostatectomy (see FIG. 1). In addition, three low-density tissue micro-arrays were used to assess for expression of EPCA in metastatic disease, high-grade PIN, normal tissue adjacent to the prostate tumors (NAT) as well as benign prostatic hyperplasia.

The staining pattern seen was both cytoplasmic and membranous. As evident from FIGS. 2 A-D, expression of EPCA was identified in patients diagnosed with carcinoma. This included the initial negative biopsy (2A), areas of high grade PIN (2B), carcinoma in the prostate (2C) as well as metastatic carcinoma in the lymph nodes (2D). Therefore, in individuals with prostate cancer, the staining occurs throughout the prostate in both NAT and tumor areas. Staining is not observed in donor prostates as well as prostate samples obtained from individuals with BPH.

Immunohistochemical Staining of Biopsy Samples

Since EPCA expression is observed throughout the prostate in individuals with prostate cancer, the inventor hypothesized that EPCA expression may allow the identification of individuals with prostate cancer even where biopsies in these individuals yield negative results by presently available diagnostic methods. In other words, the goal was to see if this protein was expressed prior to the diagnosis of prostate carcinoma by conventional methods. For this reason, negative biopsies were into the study set. If EPCA were a "field effect" marker for prostate carcinoma, then it should be possible to predict the development of clinical adenocarcinoma from a single prostate biopsy. To test the inventor's hypothesis, a test set was constructed consisting of 25 cases comprising individuals with prior negative biopsies, 0-5 years prior to having prostate carcinoma documented on a repeat biopsy. Also, the radical prostatectomy specimens were evaluated from these individuals, performed after a positive biopsy.

The median difference in calendar years between the negative biopsy and the positive biopsy was 1 year, with a range of 0 to 5 years. The positive biopsies and prostatectomies were all within the same calendar year (n=17) or 1 calendar year apart (n=8).

The donor case set, age 40 years or more, consisted of 9 cases. The donors demonstrated a significant negative correlation between the staining intensity and age (r=−0.39, p=0.05). This negative correlation with age implies that, if older donors were available, lower staining results would be expected for those donors. This would lead to an even more significant difference between donors and biopsy patients. No significant correlation was found between age and staining intensity for any of the tissue sets in the patients with prostate carcinoma.

The racial characteristics were known in 13 patients (9 Caucasians and 4 African Americans) and 18 donors (17 Caucasians and 1 African American). The donor set consisted of only one African American, so the significance of race could not be assessed in the donor case set. No race related statistical significance was seen in the staining pattern in any of the tissue sets in the patient group.

The staining intensities varied within and between case types. The case type data and the staining intensity in the different surgical materials are presented in Table 3. The abbreviations used denote negative biopsy as −Bx and positive biopsy as +Bx.

(with significantly higher score seen in the negative biopsy) using the rank-sum test (=non-parametric unpaired t-test).

The staining intensities were also compared between the negative biopsies and the normal tissues of the positive biopsy. Using the signed-rank test (=non-parametric paired t-test), there was no significant difference (p=0.74) between the negative biopsy and the normal tissue of the positive biopsy.

Figure 4:
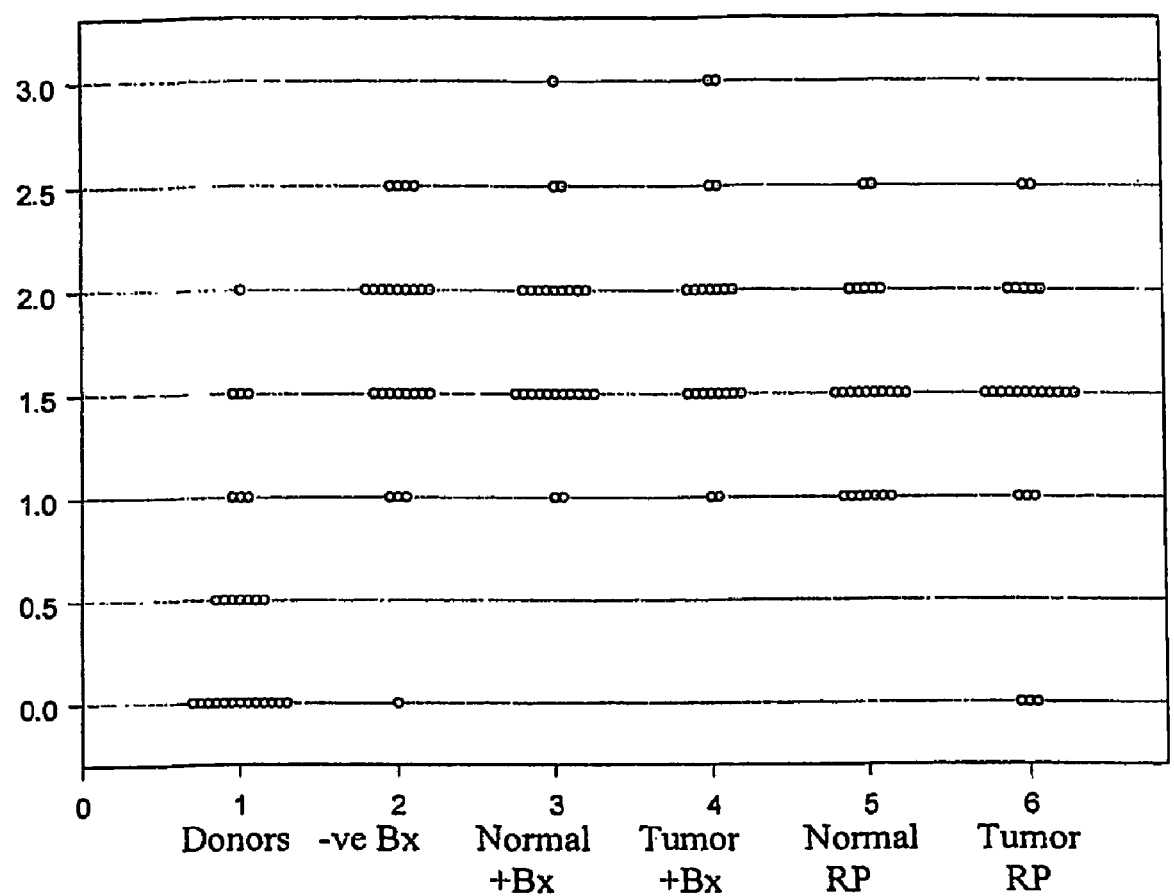
FIG. 4 shows a box plot of staining distribution.

A comparison of the staining intensities seen in the normal tissues of the positive biopsy and the tumor tissue was also performed. This revealed a significant difference (p=0.05) using the signed-rank test (=nonparametric paired t-test). This implies that EPCA upregulation carries on in the neoplastic transformation process. The dot plot (FIG. 4) displays the raw data for each tissue type, where each dot represents a single tissue sample. This display illustrates the high concentration of staining results below 1+ for the donors and the high concentration above 1+ for the other tissue types. The relatively small degree of overlap (between donor and biopsy samples) illustrates the subsequently high sensitivity and specificity for the biomarker.

To determine if staining differences existed between cancers with varying degrees of metastatic ability, the cases with positive margins were compared with the cases with negative margins. There was no significant difference in the levels of EPCA expression between the two sets. The amount of tumor seen in the prostate (% of the prostate involved by tumor) was also not significantly different for the two sets. The prostates in the margin positive group had a mean weight of 41.4 gms

TABLE 3

Staining intensity distribution for different case and tissue types

| Stain Intensity | Donors (n = 27) | Normal −Bx (n = 25) | Normal +Bx (n = 25) | Tumor +Bx (n = 21) | Normal in RP. (n = 24) | Tumor in RP (n = 25) |
|---|---|---|---|---|---|---|
| 0   | 13 | 1 | 0  | 0 | 0  | 3  |
| 0-1 | 7  | 0 | 0  | 0 | 0  | 0  |
| 1   | 3  | 3 | 2  | 2 | 7  | 3  |
| 1-2 | 3  | 8 | 11 | 8 | 10 | 12 |
| 2   | 1  | 9 | 9  | 7 | 5  | 5  |
| 2-3 | 0  | 4 | 2  | 2 | 2  | 2  |
| 3   | 0  | 0 | 1  | 2 | 0  | 0  |

The donors typically showed absent or low staining intensities (FIG. 3A). The donor set showed staining intensity greater than 1+ staining in 4 cases. These cases were completely benign and were younger individuals (15-, 17-, and 26-year old). The donor cases with prostate pathology consisted of a 63-year-old patient with established high grade PIN (FIGS. 3B and 3C) (staining intensity of 1+-2+) and a 46-year-old patient with an intermediate grade PIN (staining intensity of 2+). These two cases were excluded from the donor set since they did not qualify as "true normals." The antibody employed in FIGS. 3A-C was raised against the peptide fragment, VSNTPLPGVFTK (SEQ ID NO:1).

Staining intensities of 1+ and less were seen in 23 of 27 donors (85.2%) while only 4 of 27 donors (14.8%) had staining intensity greater than 1+. In contrast, 4 of 25 negative biopsies (16%) had staining intensities of 1+ and less while 21 of 25 negative biopsies (84%) stained strongly with staining intensity greater than 1+. Statistical comparison was performed of the staining intensities seen for EPCA in the donor prostates and compared to that in the negative biopsies. The two distributions were significantly different, with p<0.001

(median=39 gms) versus 58.1 gms (median=55.5 gms) in the margin negative cases. This difference was statistically different (with p value of 0.05).

In summary, the statistical analysis of staining intensities revealed significant differences between the donors and all the other tissue types (negative biopsies, normal and tumor tissues from the positive biopsies and normal and tumor tissues from the RP specimens). P-values for pair-wise comparisons between donors and each of the other tissue groups (using the rank-sum test=nonparametric unpaired t-test) showed all 5 comparisons to be significant at P<0.001. The overall pattern of staining for EPCA demonstrates a significant increase in staining in the negative biopsies as well as in the non-neoplastic and neoplastic tissue of the positive biopsies and RP. This contrasts with the staining pattern in the organ donor prostates, where minimal staining was identified.

This data reveals that EPCA is not typical of prior known biomarkers for prostate cancer in that it is expressed throughout the prostate in individuals with prostate cancer. It is not expressed in individuals without the disease including those with BPH and organ donors. A very significant finding is that high levels of EPCA were detected in the initial negative biopsies of men subsequently detected to have prostate cancer by biopsy. Furthermore, similar levels of EPCA are seen in the non-neoplastic tissue adjacent to tumor in the positive biopsies as well as in the radical prostatectomies. The foci of prostatic adenocarcinoma showed even higher levels of EPCA expression.

An EPCA staining intensity greater than 1+ has 84% sensitivity. Twenty-one of twenty-five patients eventually documented to have prostate cancer cases had a staining level greater than 1+ on their normal negative biopsy. An EPCA staining intensity greater than 1+ has 85% specificity. Twenty-three of twenty-seven donors had EPCA staining of 1+ or less.

Detection of EPCA in Human Plasma

Data was obtained demonstrating that it is possible to detect a protein that appears to be EPCA or a fragment of EPCA in crude plasma. Utilizing immunoblot analysis, plasma samples were probed that were obtained from individuals with advanced prostate cancer (P), prostatectomy patients (Ca) as well as age matched organ donors (D).

Figure 5:
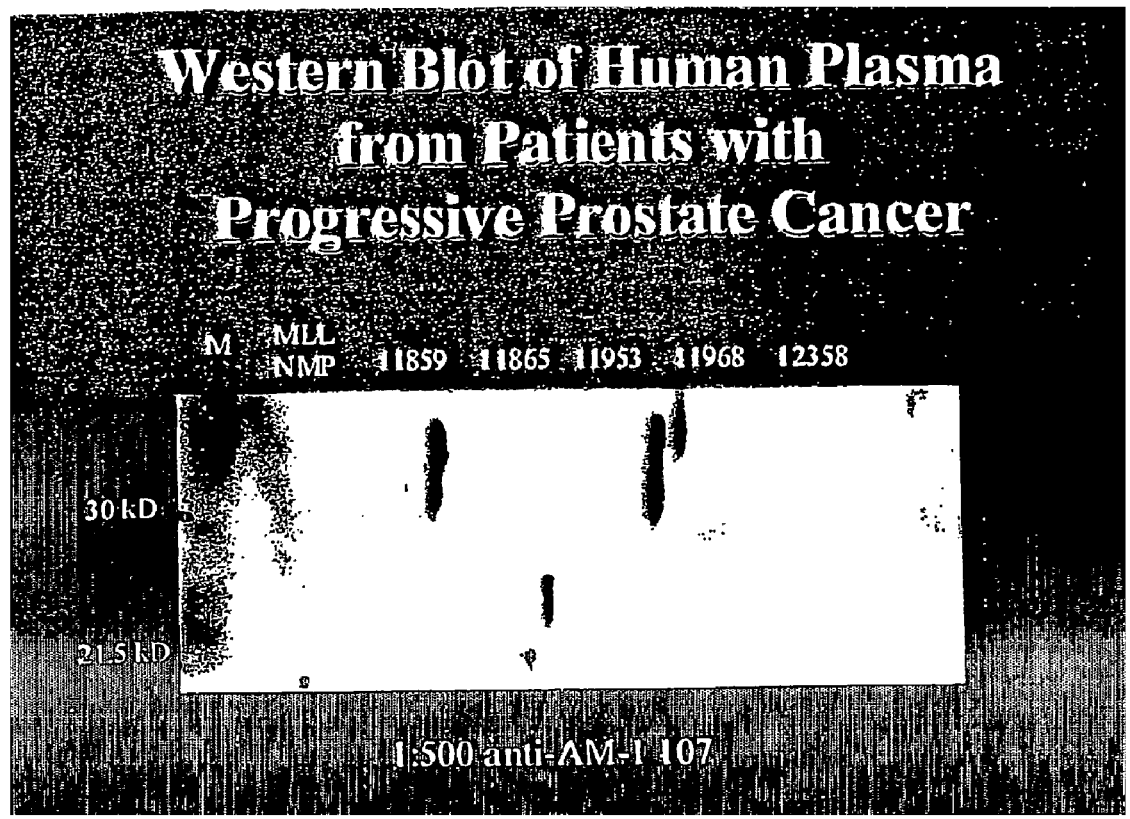
FIG. 5 shows staining of EPCA in plasma of patients with progressive prostate cancer.

In this analysis, a protein was detected in 4 out of 6 of the cancer patients and 0 out of 3 of the organ donors (FIG. 5). All of the patients with metastatic disease were identified as positive while out of the men who underwent prostatectomy, 1 of 3 was positive. It is possible that the one individual that underwent prostatectomy for localized disease actually had metastatic disease. This resulting positive band is smaller than what was found in tissue samples and could indicate that it has been cleaved in the plasma.

Sequencing of Human EPCA

Human EPCA nucleic acid and polypeptide sequences are obtained as follows. Degenerate nucleic acid primers are designed using the rat EPCA polypeptide sequences described above. These primers are used in PCR amplification methods to obtain human EPCA cDNA, which is isolated and sequenced by standard protocols. Human EPCA polypeptide sequences are derived from the cDNA sequences. Two examples are EFSGREFALVSNTPLPGVLTKKGEFV*TCRTSPFSEG* F*AWRNHGHSCFLCEIVIRSQF HTT (SEQ ID NO:5) and EFSGREFALVSNTPLPGVLTKKGEFV*TCRTSPFSEG* F*AWRNHGHSCFLCEIVIRSQF HTTYEPEA*SVKPGVPNE*ANSH*LRCAHCPLSSRET CRASCINESANARGEAVCVLG ALPLPRSLTRCARSFGCGERYQLTQRR*YGYPQNQG ITQERTCEQKASKRPGTVKRP RCWRFSIGSAPLTSITKIDAQVRGGETRQGL*RYQAF PPGSSLVRSPVPTPAAYRIPVR LSPFGKRGAFS*LTL*VSQFGVGRSLQLGCVHPVQP DAAPYP (SEQ ID NO:6), where * represents any amino acid.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All of publications, patent applications and patents cited in this specification are herein incorporated in their entirety by reference to the same extent as if each is individually incorporated by reference.

What is claimed is:

1. A method of diagnosing prostate cancer in a subject comprising (a) contacting a biological fluid sample or prostatic tissue specimen from the subject with an antibody which binds to SEQ ID NO: 1;(b) detecting binding of the antibody in the specimen; and (c) correlating the detected binding to prostate cancer.

2. The method of claim 1, wherein the specimen is a prostatic tissue sample.

3. The method of claim 1, wherein the biological fluid sample is plasma.

4. The method of claim 1, wherein the biological fluid sample is selected from among the group consisting of blood, urine, semen, and seminal fluid.

5. The method of claim 1, wherein the biological fluid sample is serum.

6. A method of diagnosing prostatic intra-epithelial neoplasia (PIN) in a subject comprising (a) contacting a plasma or prostatic tissue specimen from the subject with an antibody which binds SEQ ID NO: 1, (b) detecting binding of the antibody in the specimen, and (c) correlating the detected binding to PIN.

* * * * *

UNITED STATES PATENT AND TRADEMARK OFFICE
CERTIFICATE OF CORRECTION

PATENT NO.        : 7,598,042 B2                                      Page 1 of 1
APPLICATION NO. : 10/514735
DATED             : October 6, 2009
INVENTOR(S)       : Robert H. Getzenberg It is certified that error appears in the above-identified patent and that said Letters Patent is hereby corrected as shown below:

STATEMENT REGARDING GOVERNMENT SPONSORED RESEARCH, column 1, line 18, "may have" should read -- has --.

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,598,042 B2  Page 1 of 1
APPLICATION NO. : 10/514735
DATED : October 6, 2009
INVENTOR(S) : Getzenberg It is certified that error appears in the above-identified patent and that said Letters Patent is hereby corrected as shown below:

(*) Notice: should read, Subject to any disclaimer, the term of this patent is extended or adjusted under 35 U.S.C. 154 (b) by 734 days.

Signed and Sealed this

Twenty-second Day of June, 2010

David J. Kappos
*Director of the United States Patent and Trademark Office*